United States Patent
Schildknecht et al.

(10) Patent No.: US 9,028,979 B2
(45) Date of Patent: May 12, 2015

(54) PHENANTHROAZOLE COMPOUNDS AS HOLE TRANSPORTING MATERIALS FOR ELECTRO LUMINESCENT DEVICES

(75) Inventors: Christian Schildknecht, Mannheim (DE); Christian Lennartz, Schifferstadt (DE); Soichi Watanabe, Mannheim (DE); Gerhard Wagenblast, Wachenheim (DE); Peter Murer, Oberwil (CH); Thomas Schäfer, Liestal (CH); Natalia Chebotareva, Hagenthal le Bas (FR); Andrea Ricci, Zürich (CH); Kristina Bardon, Waldshut (DE)

(73) Assignee: BASF SE, Ludwigshafen (DE)

( * ) Notice: Subject to any disclaimer, the term of this patent is extended or adjusted under 35 U.S.C. 154(b) by 693 days.

(21) Appl. No.: 13/378,878

(22) PCT Filed: Jun. 11, 2010

(86) PCT No.: PCT/EP2010/058194
§ 371 (c)(1),
(2), (4) Date: Mar. 9, 2012

(87) PCT Pub. No.: WO2010/145991
PCT Pub. Date: Dec. 23, 2010

(65) Prior Publication Data
US 2012/0168731 A1    Jul. 5, 2012

(30) Foreign Application Priority Data
Jun. 18, 2009   (EP) ..................... 09163085

(51) Int. Cl.
| | | |
|---|---|---|
| H01L 51/54 | (2006.01) | |
| C07D 235/02 | (2006.01) | |
| C07D 403/14 | (2006.01) | |
| H01L 51/00 | (2006.01) | |
| H01L 51/50 | (2006.01) | |

(52) U.S. Cl.
CPC ............ *C07D 235/02* (2013.01); *C07D 403/14* (2013.01); *H01L 51/0061* (2013.01); *H01L 51/0072* (2013.01); H01L 51/0081 (2013.01); H01L 51/5048 (2013.01); H01L 51/5052 (2013.01); H01L 51/5096 (2013.01); Y10S 428/917 (2013.01)

(58) Field of Classification Search
CPC ............... C07D 235/02; C07D 403/14; H01L 51/0061; H01L 51/0072; H01L 51/5096; H01L 51/0081; H01L 51/5048; H01L 51/5052
See application file for complete search history.

(56) References Cited

U.S. PATENT DOCUMENTS

| | | | |
|---|---|---|---|
| 4,356,429 A | 10/1982 | Tang | |
| 4,539,507 A | 9/1985 | VanSlyke et al. | |
| 4,720,432 A | 1/1988 | VanSlyke et al. | |
| 4,768,292 A | 9/1988 | Manzei | |
| 4,769,292 A | 9/1988 | Tang et al. | |
| 4,885,211 A | 12/1989 | Tang et al. | |
| 4,885,221 A | 12/1989 | Tsuneeda | |
| 5,059,861 A | 10/1991 | Littman et al. | |
| 5,059,862 A | 10/1991 | VanSlyke et al. | |
| 5,141,671 A | 8/1992 | Bryan et al. | |
| 5,150,006 A | 9/1992 | VanSlyke et al. | |
| 5,151,629 A | 9/1992 | VanSlyke | |
| 5,247,190 A | 9/1993 | Friend et al. | |
| 5,276,380 A | 1/1994 | Tang | |
| 5,294,870 A | 3/1994 | Tang et al. | |
| 5,405,709 A | 4/1995 | Littman et al. | |
| 5,484,922 A | 1/1996 | Moore et al. | |
| 5,593,788 A | 1/1997 | Shi et al. | |
| 5,608,287 A | 3/1997 | Hung et al. | |
| 5,645,948 A | 7/1997 | Shi et al. | |

(Continued)

FOREIGN PATENT DOCUMENTS

| | | |
|---|---|---|
| EP | 0 732 868 | 9/1996 |
| EP | 0 891 121 | 1/1999 |

(Continued)

OTHER PUBLICATIONS

U.S. Appl. No. 14/123,530, filed Dec. 3, 2013, Koenemann, et al.

(Continued)

*Primary Examiner* — Dawn L. Garrett
(74) *Attorney, Agent, or Firm* — Oblon, McClelland, Maier & Neustadt, L.L.P.

(57) ABSTRACT

The present invention relates to electroluminescent devices, comprising a compound of the formula (I) as a component of the transporting/injecting and/or electron blocking layer. The compounds of formula (I) may function alone, or in combination with dopants to provide improved efficiency, driving voltage and/or lifetime of electroluminescent devices.

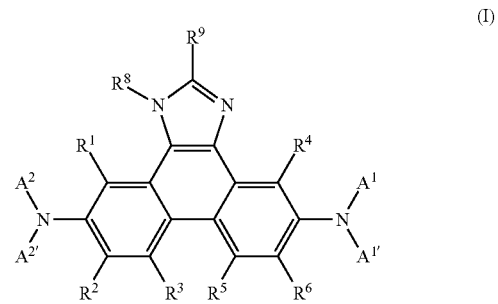

(I)

17 Claims, No Drawings

(56) References Cited

U.S. PATENT DOCUMENTS

| | | |
|---|---|---|
| 5,677,572 A | 10/1997 | Hung et al. |
| 5,683,823 A | 11/1997 | Shi et al. |
| 5,688,551 A | 11/1997 | Littman et al. |
| 5,703,436 A | 12/1997 | Forrest et al. |
| 5,714,838 A | 2/1998 | Haight et al. |
| 5,739,545 A | 4/1998 | Guha et al. |
| 5,755,999 A | 5/1998 | Shi et al. |
| 5,776,622 A | 7/1998 | Hung et al. |
| 5,776,623 A | 7/1998 | Hung et al. |
| 5,837,391 A | 11/1998 | Utsugi |
| 5,851,709 A | 12/1998 | Grande et al. |
| 5,928,802 A | 7/1999 | Shi et al. |
| 5,935,720 A | 8/1999 | Chen et al. |
| 5,935,721 A | 8/1999 | Shi et al. |
| 5,969,474 A | 10/1999 | Arai |
| 5,981,306 A | 11/1999 | Burrows et al. |
| 6,020,078 A | 2/2000 | Chen et al. |
| 6,066,357 A | 5/2000 | Tang et al. |
| 6,097,147 A | 8/2000 | Baldo et al. |
| 6,137,223 A | 10/2000 | Hung et al. |
| 6,140,763 A | 10/2000 | Hung et al. |
| 6,172,459 B1 | 1/2001 | Hung et al. |
| 6,208,075 B1 | 3/2001 | Hung et al. |
| 6,226,890 B1 | 5/2001 | Boroson et al. |
| 6,278,236 B1 | 8/2001 | Madathil et al. |
| 6,337,102 B1 | 1/2002 | Forrest et al. |
| 6,413,656 B1 | 7/2002 | Thompson et al. |
| 6,451,415 B1 | 9/2002 | Forrest et al. |
| 6,451,455 B1 | 9/2002 | Thompson et al. |
| 6,458,475 B1 | 10/2002 | Adachi et al. |
| 6,515,298 B2 | 2/2003 | Forrest et al. |
| 6,573,651 B2 | 6/2003 | Adachi et al. |
| 7,090,930 B2 | 8/2006 | Robello et al. |
| 2002/0100906 A1 | 8/2002 | Takiguchi et al. |
| 2002/0117662 A1 | 8/2002 | Nii |
| 2002/0121638 A1 | 9/2002 | Grushin et al. |
| 2002/0197511 A1 | 12/2002 | D'Andrade et al. |
| 2003/0017361 A1 | 1/2003 | Thompson et al. |
| 2003/0040627 A1 | 2/2003 | Fujii |
| 2003/0054198 A1 | 3/2003 | Tsuboyama et al. |
| 2003/0059646 A1 | 3/2003 | Kamatani et al. |
| 2003/0068526 A1 | 4/2003 | Kamatani et al. |
| 2003/0068528 A1 | 4/2003 | Thompson et al. |
| 2003/0068535 A1 | 4/2003 | Takiguchi et al. |
| 2003/0072964 A1 | 4/2003 | Kwong et al. |
| 2003/0124381 A1 | 7/2003 | Thompson et al. |
| 2003/0141809 A1 | 7/2003 | Furugori et al. |
| 2003/0175553 A1 | 9/2003 | Thompson et al. |
| 2006/0289882 A1 | 12/2006 | Nishimura et al. |
| 2007/0029927 A1 | 2/2007 | Kawamura et al. |
| 2008/0171228 A1 | 7/2008 | Chen et al. |
| 2008/0265216 A1 | 10/2008 | Hartmann et al. |
| 2010/0039024 A1 | 2/2010 | Wendeborn et al. |
| 2010/0109514 A1 | 5/2010 | Schaefer et al. |

FOREIGN PATENT DOCUMENTS

| | | |
|---|---|---|
| EP | 1 029 909 | 8/2000 |
| EP | 1 076 368 | 2/2001 |
| EP | 1 238 981 | 9/2002 |
| EP | 1 239 526 | 9/2002 |
| EP | 1 244 155 | 9/2002 |
| EP | 1 596 445 | 11/2005 |
| JP | 2 134644 | 5/1990 |
| JP | 3 234963 | 10/1991 |
| JP | 9 13025 | 1/1997 |
| JP | 11 251063 | 9/1999 |
| JP | 2000 323278 | 11/2000 |
| JP | 2001 23777 | 1/2001 |
| JP | 2001 118683 | 4/2001 |
| JP | 2002 50473 | 2/2002 |
| JP | 2002 367786 | 12/2002 |
| JP | 2003 59667 | 2/2003 |
| JP | 2003 59670 | 2/2003 |
| JP | 2003 73387 | 3/2003 |
| JP | 2003 73388 | 3/2003 |
| JP | 2003 73665 | 3/2003 |
| JP | 2006 143845 | 6/2006 |
| WO | 00 57676 | 9/2000 |
| WO | 00 70655 | 11/2000 |
| WO | 01 39234 | 5/2001 |
| WO | 01 41512 | 6/2001 |
| WO | 01 93642 | 12/2001 |
| WO | 02 15645 | 2/2002 |
| WO | 02 071813 | 9/2002 |
| WO | 02 074015 | 9/2002 |
| WO | 2006 000544 | 1/2006 |
| WO | 2006 097419 | 9/2006 |
| WO | 2008 031743 | 3/2008 |
| WO | 2008 058525 | 5/2008 |
| WO | 2008 101842 | 8/2008 |
| WO | 2008 119666 | 10/2008 |
| WO | 2008 138580 | 11/2008 |
| WO | 2009 003455 | 1/2009 |

OTHER PUBLICATIONS

U.S. Appl. No. 13/516,117, filed Aug. 27, 2012, Molt, et al.
U.S. Appl. No. 14/115,934, filed Nov. 6, 2013, Wagenblast, et al.
International Search Report Issued Sep. 16, 2010 in PCT/EP10/58194 Filed Jun. 11, 2010.
U.S. Appl. No. 13/352,482, filed Oct. 4, 2011, Schaefer, et al.

PHENANTHROAZOLE COMPOUNDS AS HOLE TRANSPORTING MATERIALS FOR ELECTRO LUMINESCENT DEVICES

CROSS REFERENCE TO RELATED APPLICATION

This application is a 371 of PCT/EP2010/058194, filed on Jun. 11, 2010, and claims priority to European Patent Application 09163085.5, filed on Jun. 18, 2009.

The present invention relates to electroluminescent devices, comprising a compound of the formula

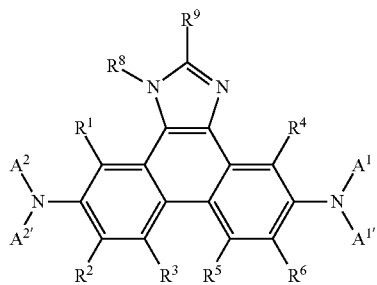

(I)

as a component of the hole transporting/injecting and/or electron blocking layer. The compounds of formula I may function alone, or in combination with dopants to provide improved efficiency, driving voltage and/or lifetime of electroluminescent devices.

JP9013025 relates to an electroluminescent element a quinoxaline derivative represented by the formula

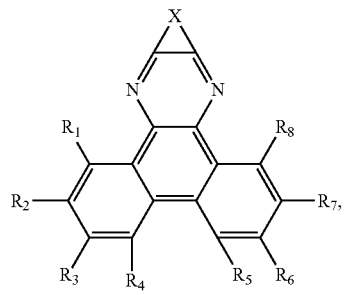

wherein X is a $C_2$-$C_5$alkyl or the like; and $R_1$ to $R_8$, which are independent of each other, are each H, a halogen, a $C_1$-$C_6$alkyl or the like.

JP11251063 discloses triphenylene compounds expressed by the formula

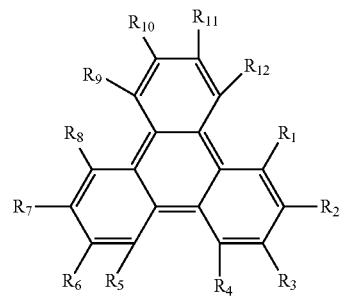

which are used as a component material of an organic EL element. In the formula, $R_1$ to $R_{12}$ each independently represent an hydrogen atom, a halogen atom, a hydroxyl group, a substituted or unsubstituted amino group, a nitro group, a cyano group, a substituted or unsubstituted alkyl group, a substituted or unsubstituted alkenyl group, a substituted or unsubstituted cycloalkyl group, a substituted or unsubstituted alkoxy group, a substituted or unsubstituted aromatic hydrocarbon group, a substituted or unsubstituted aromatic heterocycle group, a substituted or unsubstituted aralkyl group, a substituted or unsubstituted aryloxy group, a substituted or unsubstituted alkoxycarbonyl group, or a carboxyl group. $R_1$ to $R_{12}$ may form two rings out of them.

JP2006143845 relates to compounds of formula

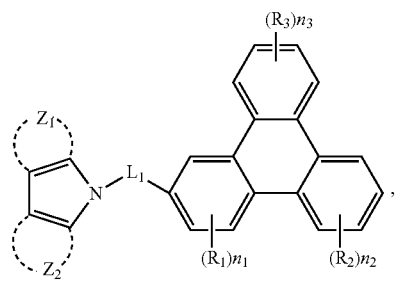

wherein $Z_1$, $Z_2$ are an aromatic hydrocarbon ring, aromatic heterocyclic ring; $R_1$ to $R_3$ are H, substituent; n1=0 to 3; n2, n3=0 to 4; L1=linkage group, single bond).

JP2134644 relates to an electrophotographic sensitive body having a phenazine compound in a photosensitive layer. The phenazine compound is expressed by formula

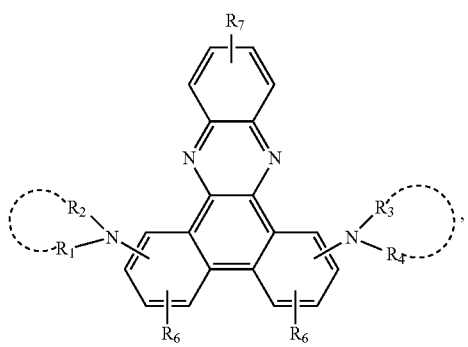

wherein each $R_1$-$R_4$ is an H atom, a (substituted)alkyl group, aralkyl group, aryl group, or heterocyclic group, wherein $R_1$ and $R_2$, and $R_3$ and $R_4$ may form a 5-7 membered ring together with an N atom, respectively; each $R_5$-$R_7$ is an H atom, (substituted)alkyl group, alkoxy group, halogen atom or nitro group.

US20060289882 relates to an organic electroluminescent device, wherein the electron extracting layer may be formed of a hexaazatriphenylene derivative represented by the following structural formula

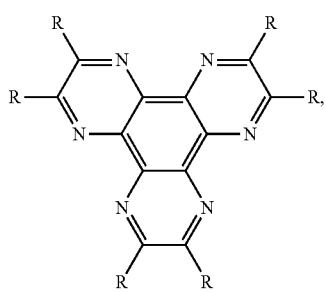

wherein R represents hydrogen, an alkyl group having a carbon number of 1 to 10, an alkyloxy group having a carbon number of 1 to 10, a dialkylamine group having a carbon number of 1 to 10, F, Cl, Br, I or CN.

US20070029927 discloses aromatic amine derivative represented by the following general formula (1):

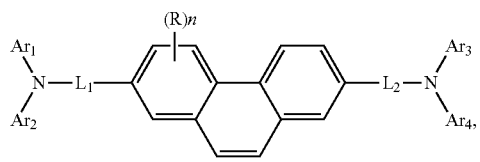

wherein $Ar_1$ to $Ar_4$ each independently represents a substituted or unsubstituted aryl group having 6 to 30 ring carbon atoms or a substituted or unsubstituted heteroaryl group having 5 to 30 ring carbon atoms;
L1 and L2 each independently represents a single bond, a substituted or unsubstituted arylene group having 6 to 30 ring carbon atoms or a substituted or unsubstituted heteroarylene group having 5 to 30 ring carbon atoms;
when both L1 and L2 are single bonds, however, a case where both $Ar_1$ and $Ar_3$ each represents a substituted or unsubstituted phenyl group and further, where both Are and Ara each represents a substituted or unsubstituted biphenylyl group or a substituted or unsubstituted phenyl group is excluded; R represents a substituent and when R exists two or more, they may bond each other to form a ring; and n represents an integer of 0 to 8 and their use in organic electroluminescence devices.

JP2134644 relates to phenazine compounds of formula

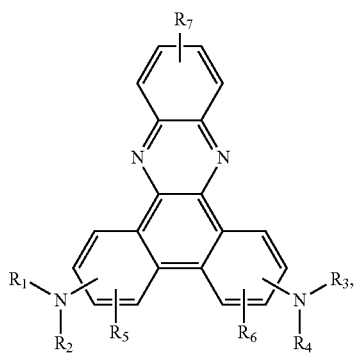

wherein each of $R_1$-$R_4$ is an H atom, a (substituted)alkyl group, aralkyl group, aryl group, or heterocyclic group, wherein $R_1$ and $R_2$, and $R_3$ and $R_4$ may form a 5-7 membered ring together with an N atom, respectively; each of $R_5$-$R_7$ is an H atom, (substituted)alkyl group, alkoxy group, halogen atom or nitro group. When the phenazine compounds are incorporated into a photosensitive layer of an electrophotographic sensitive body.

JP2000323278 relates to an emitter including an organic phosphor having an imidazole structure of the formula

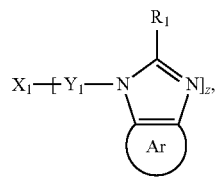

wherein $R_1$ may be either same or different respectively and selected from hydrogen, an alkyl group, a cycloalkyl group, an aralkyl group, an alkenyl group, a cycloalkenyl group, etc., $X_1$ is a bonding unit and selected from a substituted or non-substituted aromatic ring, heterocycle, a saturated fat chain, etc., $Y_1$ is selected from a single bond or a combination of either of single bond, an alkyl chain, an alkylene chain, an ether chain, etc., and Ar is selected from a substituted or non-substituted aromatic ring, heterocycle, etc. and z expresses a natural number. The organic phosphor is preferably a light emitting material having a guest material doped in a host material.

JP 2001023777 describes compounds of the formula

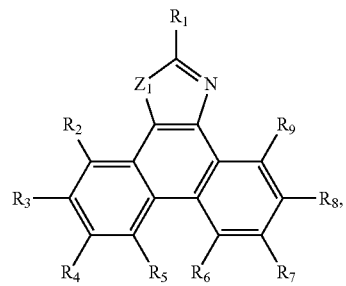

wherein $R_1$ to $R_9$ represent bonding, hydrogen, an alkyl group, a cycloalkyl group, an aralkyl group, an alkenyl group, a cycloalkenyl group, an alkoxy group, an alkylthio group, an arylether group, an aryl thioether group, an aryl group, a heterocyclic group, halogen, a cyano group, an aldehyde group, a carbonyl group, an ester group, a carbamoyl group, an amino group, a nitro group, a silyl group, a siloxyanyl group, and ring structure formed between adjacent substituting groups, and $Z_1$ represents oxygen, sulfur, nitrogen, or saturated hydrocarbon. The compounds having a phenanthroazole skeleton are suitable as a host material or a dopant material in a material of a hole transport layer, an electron transport layer, and a luminescent layer. No compounds, wherein any of $R_1$ to $R_9$ is an aryl substituted amino group are disclosed.

JP2001118683 relates to a luminescent element, wherein the luminescent material is at least composed of a guest material and a host material and the peak of the emission spectrum of the host material is more than 300 nm and less than 460 nm. The following phenanthroazole compound is explicitly disclosed:

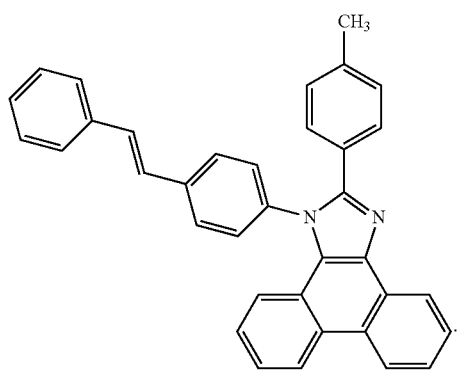 [SMILES: Cc1ccc(-c2nc3c4ccccc4c4ccccc4c3n2-c2ccc(/C=C/c3ccccc3)cc2)cc1]

JP2002050473 describes an element, in which a light emitting substance exists between a positive electrode and a negative electrode and which emits light by electric energy, and the element contains at least one kind of product formed by a photoreaction. The following phenanthroazole compound is explicitly disclosed:

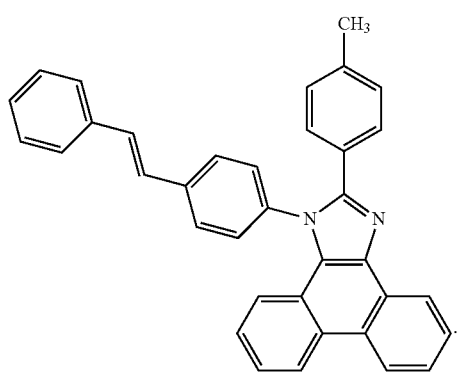 [SMILES: Cc1ccc(-c2nc3c4ccccc4c4ccccc4c3n2-c2ccc(/C=C/c3ccccc3)cc2)cc1]

JP2003059670 describes a light-emitting element having a structure in which at least a positive electrode, a luminous layer, an electron carrier layer, and a negative electrode are laminated in order, the electron carrier layer has an ionization potential 0.1 eV or more larger than the ionization potential of the luminous layer, and the material that mainly constitutes the luminous layer and the electron carrier layer is made of an organic compound having sublimation performance, and further, the organic compound that mainly constitutes the electron carrier layer has a molecular weight of 400 or more and a glass transition temperature of 90° C. or more. The following phenanthroazole compound is explicitly disclosed:

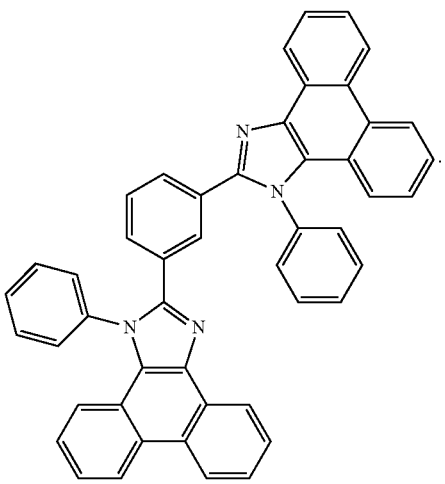 [SMILES: c1ccc(-n2c(-c3cccc(-c4nc5c6ccccc6c6ccccc6c5n4-c4ccccc4)c3)nc3c4ccccc4c4ccccc4c32)cc1]

JP2002367786 describes a luminous element having a sequentially laminated structure of at least a positive electrode, a luminous layer, a hole transport layer, an electron transport layer and a negative electrode, the relation between the luminous layer and the electron transport layer is (Ip(ETL)−Ip(EML))>(Ea(ETL)−Ea(EML)). The main material composing the luminous layer and the electron transport layer is made of an organic compound with sublimatic nature, and the main material composing the electron transport layer is an organic compound with molecular mass of not less than 400. [Ea: electron affinity (eV), Ip: ionization potential (eV), EML: luminous layer, and ETL: electron transport layer]. The following phenanthroazole compound is explicitly disclosed:

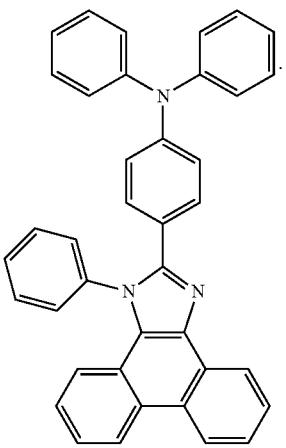 [SMILES: c1ccc(N(c2ccccc2)c2ccc(-c3nc4c5ccccc5c5ccccc5c4n3-c3ccccc3)cc2)cc1]

WO08/031743 describes electroluminescent devices, comprising a compound of the formula

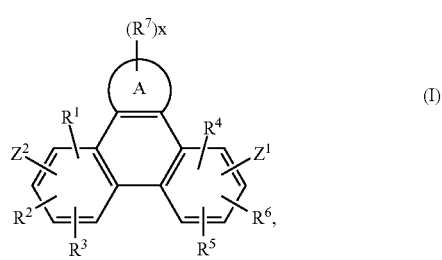

(I)

especially as host for phosphorescent compounds. The hosts may function with phosphorescent materials to provide improved efficiency, stability, manufacturability, or spectral characteristics of electroluminescent devices.

Notwithstanding these developments, there remains a need for EL devices comprising materials for hole transporting materials that will function to provide improved efficiency, stability, manufacturability, or spectral characteristics of electroluminescent devices, especially as an material for an electron blocking layer and/or an optionally doped hole transporting/injecting layer, which provides improved efficiency, driving voltage and/or lifetime.

Accordingly, the present invention provides an electroluminescent (EL) device, comprising an anode, a hole transporting/injecting layer, optionally an electron blocking layer, a light-emitting layer, optionally a hole- or exciton-blocking layer, an electron-transporting layer, and a cathode, characterized in that the hole transporting/injecting layer and/or the electron blocking layer comprises a compound of the formula

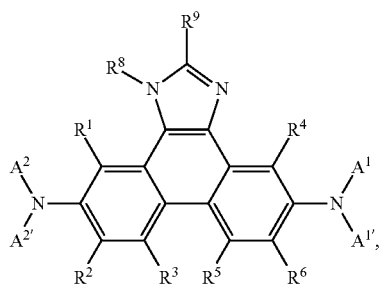

(I)

wherein $R^1$ and $R^4$ are independently of each other hydrogen, $C_1$-$C_{10}$alkyl, $C_1$-$C_{18}$alkyl which is substituted by E and/or interrupted by D, $C_1$-$C_{18}$perfluoroalkyl, $C_2$-$C_{18}$alkenyl, $C_2$-$C_{10}$alkynyl, $C_1$-$C_{10}$alkoxy, $C_1$-$C_{18}$alkoxy which is substituted by E and/or interrupted by D, CN, or —CO—$R^{28}$, $R^2$, $R^3$, $R^5$ and $R^6$ are independently of each other H, $C_1$-$C_{18}$alkyl, $C_1$-$C_{10}$alkyl which is substituted by E and/or interrupted by D, $C_1$-$C_{18}$perfluoroalkyl, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{10}$alkynyl, $C_1$-$C_{18}$alkoxy, $C_1$-$C_{18}$alkoxy which is substituted by E and/or interrupted by D, $C_7$-$C_{25}$aralkyl, CN, or —CO—$R^{28}$, $R^8$ is $C_1$-$C_{18}$alkyl, $C_1$-$C_{18}$alkyl which is substituted by E and/or interrupted by D, $C_1$-$C_{18}$perfluoroalkyl, $C_6$-$C_{24}$aryl, $C_6$-$C_{24}$aryl which is substituted by G, $C_2$-$C_{20}$heteroaryl, or $C_2$-$C_{20}$heteroaryl which is substituted by G, $R^9$ is H, $C_1$-$C_{18}$alkyl, $C_1$-$C_{18}$alkyl which is substituted by E and/or interrupted by D, $C_1$-$C_{18}$perfluoroalkyl, $C_6$-$C_{24}$aryl, $C_6$-$C_{24}$aryl which is substituted by G, $C_2$-$C_{20}$heteroaryl, or $C_2$-$C_{20}$heteroaryl which is substituted by G, two substituents $R^2$ and $R^3$, and/or $R^5$ and $R^6$, which are adjacent to each other, together form a group

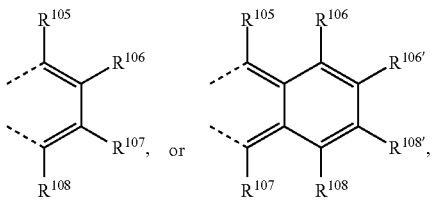

$R^{105}$, $R^{106}$, $R^{107}$, $R^{108}$, $R^{106'}$ and $R^{108'}$ are independently of each other H, $C_1$-$C_{18}$alkyl, $C_1$-$C_{18}$alkyl which is substituted by E and/or interrupted by D, $C_1$-$C_{18}$alkoxy, or $C_1$-$C_{18}$alkoxy which is substituted by E and/or interrupted by D, and $A^1$, $A^2$, $A^{1'}$ and $A^{2'}$ are independently of each other a group of formula

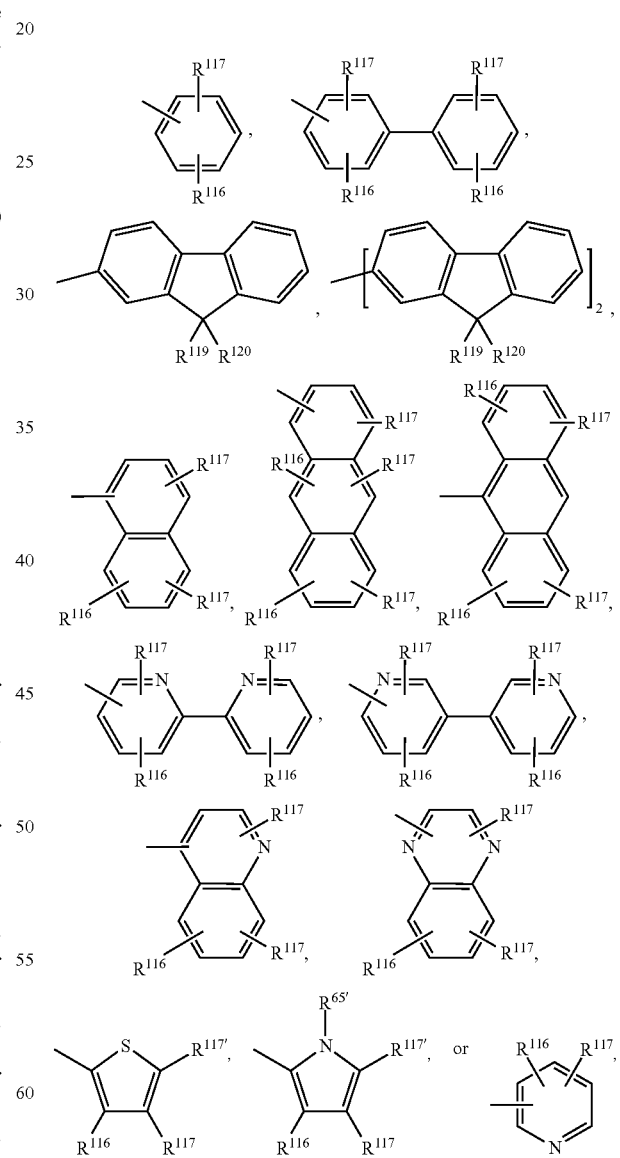

or $A^1$ and $A^{1'}$, and/or $A^2$ and $A^{2'}$ together with the nitrogen atom to which they are bonded form a heteroaromatic ring, or ring system, such as

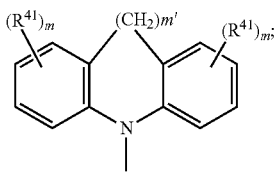

m' is 0, 1, or 2;
m can be the same or different at each occurrence and is 0, 1, 2, or 3, especially 0, 1, or 2, very especially 0, or 1;
$R^{41}$ can be the same or different at each occurrence and is Cl, F, CN, $N(R^{45})_2$, a $C_1$-$C_{25}$alkyl group, a $C_4$-$C_{18}$cycloalkyl group, a $C_1$-$C_{25}$alkoxy group, in which one or more carbon atoms which are not in neighbourhood to each other could be replaced by $-NR^{45}-$, $-O-$, $-S-$, or $-C(=O)-O-$, and/or wherein one or more hydrogen atoms can be replaced by F, a $C_6$-$C_{24}$aryl group, or a $C_6$-$C_{24}$aryloxy group, wherein one or more carbon atoms can be replaced by O, S, or N, and/or which can be substituted by one or more non-aromatic groups $R^{41}$, or two or more groups $R^{41}$ form a ring system;
$R^{45}$ is H, a $C_1$-$C_{25}$alkyl group, a $C_4$-$C_{18}$cycloalkyl group, in which one or more carbon atoms which are not in neighbourhood to each other could be replaced by $-NR^{45''}-$, $-O-$, $-S-$, $-C(=O)-O-$, or, $-O-C(=O)-O-$, and/or wherein one or more hydrogen atoms can be replaced by F, a $C_6$-$C_{24}$aryl group, or a $C_6$-$C_{24}$aryloxy group, wherein one or more carbon atoms can be replaced by O, S, or N, and/or which can be substituted by one or more non-aromatic groups $R^{41}$, and
$R^{45''}$ is H, a $C_1$-$C_{25}$alkyl group, or a $C_4$-$C_{18}$cycloalkyl group,
$R^{65'}$ is H, a $C_1$-$C_{25}$alkyl group, a $C_4$-$C_{18}$cycloalkyl group, in which one or more carbon atoms which are not in neighbourhood to each other could be replaced by $-O-$, or $-S-$, and/or wherein one or more hydrogen atoms can be replaced by F, a $C_6$-$C_{24}$aryl group, or a $C_6$-$C_{24}$aryloxy group, wherein one or more carbon atoms can be replaced by O, S, or N, and/or which can be substituted by G,
$R^{116}$, $R^{117}$ and $R^{117'}$ are independently of each other H, halogen, $-CN$, $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, $C_7$-$C_{25}$aralkyl, $-C(=O)-R^{127'}$, $-C(=O)OR^{127'}$, or $-C(=O)NR^{127'}R^{126}$, or substituents $R^{116}$, $R^{117}$ and $R^{117'}$, which are adjacent to each other, can form a ring,
$R^{119}$ and $R^{120}$ are independently of each other $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, or $C_7$-$C_{25}$aralkyl, or
$R^{119}$ and $R^{129}$ together form a group of formula $=CR^{121}R^{122}$, wherein
$R^{121}$ and $R^{122}$ are independently of each other H, $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, or $C_2$-$C_{20}$heteroaryl, or $C_2$-$C_{20}$heteroaryl which is substituted by G, or
$R^{119}$ and $R^{120}$ together form a five or six membered ring, which optionally can be substituted by $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, $C_7$-$C_{25}$aralkyl, or $-C(=O)-R^{127'}$, and
$R^{126}$, $R^{127}$ and $R^{127'}$ are independently of each other $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by $-O-$,
D is $-CO-$; $-COO-$; $-S-$; $-SO-$; $-SO_2-$; $-O-$; $-NR^{25}-$; $-SiR^{30}R^{31}-$; $-POR^{32}-$; $-CR^{23}=CR^{24}-$; or $-C\equiv C-$; and
E is $-OR^{29}$; $-SR^{29}$; $-NR^{25}R^{26}$; $-COR^{28}$; $-COOR^{27}$; $-CONR^{25}R^{26}$; $-CN$; or halogen; G is E, $C_1$-$C_{18}$alkyl which is interrupted by D, $C_1$-$C_{18}$perfluoroalkyl, $C_1$-$C_{18}$alkoxy, or $C_1$-$C_{18}$alkoxy which is substituted by E and/or interrupted by D, wherein
$R^{23}$ and $R^{24}$ are independently of each other $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by $-O-$;
$R^{25}$ and $R^{26}$ are independently of each other $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by $-O-$; or
$R^{25}$ and $R^{26}$ together form a five or six membered ring, $R^{27}$ and $R^{28}$ are independently of each other $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by $-O-$,
$R^{29}$ is $C_6$-$C_{18}$aryl; $C_6$-$C_{18}$aryl, which is substituted by $C_1$-$C_{18}$alkyl, or $C_1$-$C_{18}$alkoxy; $C_1$-$C_{18}$alkyl; or $C_1$-$C_{18}$alkyl which is interrupted by $-O-$,
$R^{30}$ and $R^{31}$ are independently of each other $C_1$-$C_{18}$alkyl, $C_6$-$C_{18}$aryl, or $C_6$-$C_{18}$aryl, which is substituted by $C_1$-$C_{18}$alkyl, and
$R^{32}$ is $C_1$-$C_{18}$alkyl, $C_6$-$C_{18}$aryl, or $C_6$-$C_{18}$aryl, which is substituted by $C_1$-$C_{18}$alkyl.

The compounds of formula I are used alone, or in combination with other materials as material (component) for the hole transporting layer of electroluminescent devices in organic light emitting diodes (OLEDs). The compounds of formula I may function alone, or in combination with dopants to provide improved efficiency, driving voltage and/or lifetime of electroluminescent devices.

Alternatively, the compounds of formula I can be used as material for the electron blocking layer. The compounds of formula I may function alone, to provide improved efficiency, driving voltage and/or lifetime of electroluminescent devices.

The term "hole transporting/injecting layer" as herein employed refers to a layer which is positioned between a light-emitting layer and an anode, preferably adjacent to the anode, and mainly injects/transports holes.

Preferably, $R^{116}$ and $R^{117}$ are independently of each other H, $C_1$-$C_{12}$alkyl, such as methyl, ethyl, n-propyl, iso-propyl, n-butyl, isobutyl, sec-butyl, t-butyl, 2-methylbutyl, n-pentyl, isopentyl, n-hexyl, 2-ethylhexyl, or n-heptyl, $C_1$-$C_{12}$alkyl which is substituted by E and/or interrupted by D, such as $-CH_2OCH_3$, $-CH_2OCH_2CH_3$, $-CH_2OCH_2CH_2OCH_3$, or $-CH_2OCH_2CH_2OCH_2CH_3$, $C_6$-$C_{14}$aryl, such as phenyl, naphthyl, or biphenylyl, $C_5$-$C_{12}$cycloalkyl, such as cyclohexyl, $C_6$-$C_{14}$aryl which is substituted by G, such as $-C_6H_4OCH_3$, $-C_6H_{40}OCH_2CH_3$, $-C_6H_3(OCH_3)_2$, or $-C_6H_3(OCH_2CH_3)_2$, $-C_6H_4-CH_3$, $-C_6H_3(CH_3)_2$, $-C_6H_2(CH_3)_3$, or $-C_6H_4tBu$.

Preferably, $R^{119}$ and $R^{120}$ are independently of each other $C_1$-$C_{12}$alkyl, such as methyl, ethyl, n-propyl, iso-propyl, n-butyl, sec-butyl, hexyl, octyl, or 2-ethyl-hexyl, $C_1$-$C_{12}$alkyl which is substituted by E and/or interrupted by D, such as —$CH_2(OCH_2CH_2)_wOCH_3$, w=1, 2, 3, or 4, $C_6$-$C_{14}$aryl, such as phenyl, naphthyl, or biphenylyl, $C_6$-$C_{14}$aryl which is substituted by G, such as —$C_6H_{40}OCH_3$, —$C_6H_{40}OCH_2CH_3$, —$C_6H_3(OCH_3)_2$, —$C_6H_3(OCH_2CH_3)_2$, —$C_6H_4$—$CH_3$, —$C_6H_3(CH_3)_2$, —$C_6H_2(CH_3)_3$, or —$C_6H_4tBu$, or $R^{119}$ and $R^{120}$ together form a 4 to 8 membered ring, especially a 5 or 6 membered ring, such as cyclohexyl, or cyclopentyl, which can optionally be substituted by $C_1$-$C_8$alkyl.

D is preferably —CO—, —COO—, —S—, —SO—, —$SO_2$—, —O—, —$NR^{25}$—, wherein $R^{25}$ is $C_1$-$C_{12}$alkyl, such as methyl, ethyl, n-propyl, iso-propyl, n-butyl, isobutyl, or sec-butyl, or $C_6$-$C_{14}$aryl, such as phenyl, tolyl, naphthyl, or biphenylyl.

E is preferably —$OR^{29}$; —$SR^{29}$; —$NR^{25}R^{25}$; —$COR^{28}$; —$COOR^{27}$; —$CONR^{25}R^{25}$; or —CN; wherein $R^{25}$, $R^{27}$, $R^{28}$ and $R^{29}$ are independently of each other $C_1$-$C_{12}$alkyl, such as methyl, ethyl, n-propyl, iso-propyl, n-butyl, isobutyl, sec-butyl, hexyl, octyl, or 2-ethyl-hexyl, or $C_6$-$C_{14}$aryl, such as phenyl, tolyl, naphthyl, or biphenylyl, which may optionally be substituted.

G has the same preferences as E, or is $C_1$-$C_{18}$alkyl, especially $C_1$-$C_{12}$alkyl, such as methyl, ethyl, n-propyl, iso-propyl, n-butyl, isobutyl, sec-butyl, hexyl, octyl, or 2-ethyl-hexyl, or is $C_1$-$C_{18}$perfluoroalkyl, such, for example, —$CF_3$.

Compounds of the formula I are even more preferred, wherein $R^1$ and $R^4$ are hydrogen, $R^2$, $R^3$, $R^5$ and $R^6$ are independently of each other H, $C_1$-$C_{18}$alkyl, $C_1$-$C_{18}$alkyl which is interrupted by D, $C_1$-$C_{18}$perfluoroalkyl, $C_1$-$C_{18}$alkoxy, $C_1$-$C_{18}$alkoxy which is interrupted by D, or $C_7$-$C_{25}$aralkyl;
$R^8$ is $C_1$-$C_{18}$alkyl, $C_1$-$C_{18}$alkyl which is interrupted by D; $C_1$-$C_{18}$perfluoroalkyl, $C_6$-$C_{18}$aryl, which may optionally be substituted by $C_1$-$C_{18}$alkyl, $C_1$-$C_{18}$perfluoroalkyl, $C_1$-$C_{18}$alkoxy, or $C_1$-$C_{18}$alkoxy, which is interrupted by D;
$R^9$ is H, $C_1$-$C_{18}$alkyl, $C_1$-$C_{18}$alkyl which is interrupted by D, $C_1$-$C_{18}$perfluoroalkyl, $C_6$-$C_{18}$aryl, which may optionally be substituted by $C_1$-$C_{18}$alkyl, $C_1$-$C_{18}$perfluoroalkyl, $C_1$-$C_{18}$alkoxy, or $C_1$-$C_{18}$alkoxy, which is interrupted by D, wherein
D is —CO—; —CaO—; —S—; —SO—; —$SO_2$—; —O—; —$NR^{25}$—; —$CR^{23}$=$CR^{24}$—; or —C≡C—; wherein $R^{23}$ and $R^{24}$ are independently of each other H; and
$R^{25}$ is $C_6$-$C_{18}$aryl; $C_6$-$C_{18}$aryl which is substituted by $C_1$-$C_8$alkyl, or $C_1$-$C_{18}$alkoxy; $C_1$-$C_8$alkyl; or $C_1$-$C_8$alkyl which is interrupted by —O—.
$R^8$ is more preferably $C_6$-$C_{18}$aryl, which may optionally be substituted by $C_1$-$C_{18}$alkyl, $C_1$-$C_{18}$perfluoroalkyl, or $C_1$-$C_{18}$alkoxy;
$R^9$ is more preferably $C_6$-$C_{18}$aryl, which may optionally be substituted by $C_1$-$C_{18}$alkyl or $C_1$-$C_{18}$perfluoroalkyl, $C_1$-$C_{18}$alkoxy, or $C_1$-$C_{18}$alkoxy which is interrupted by D.
D is —S—, —O—, or —$NR^{25}$—,
$R^{25}$ is $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—.

In a preferred embodiment of the present invention $R^1$, $R^2$, $R^3$, $R^4$, $R^5$ and $R^6$ are hydrogen. Examples of

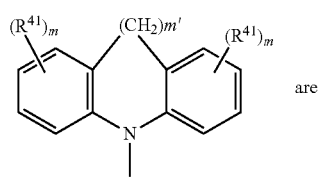 are

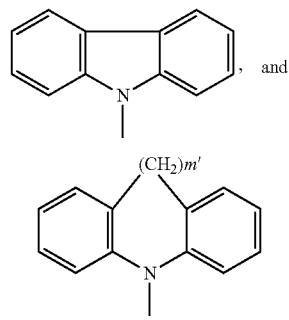 and ($m'$ = 2).

Preferably, $A^1$, $A^2$, $A^{1'}$ and $A^{2'}$ are independently of each other a group of formula

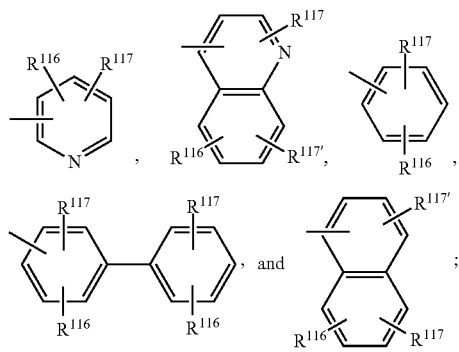

more preferably $A^1$, $A^2$, $A^{1'}$ and $A^{2'}$ are independently of each other a group of formula

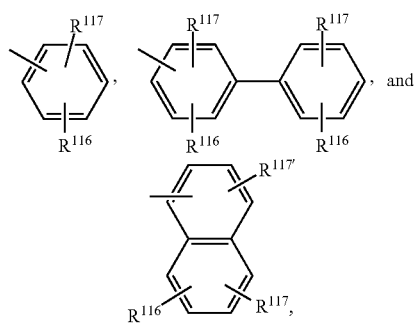

$A^1$ and $A^{1'}$ and/or $A^2$ and $A^{2'}$ together with the nitrogen atom to which they are bonded form a group of formula

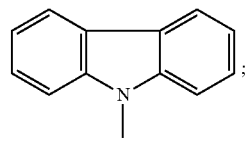

wherein $R^{116}$, $R^{117}$ and $R^{117'}$ are independently of each other H, or $C_1$-$C_{18}$alkyl. Specific examples of $A^1$, $A^2$, $A^1$ and $A^{2'}$ are Preferably, $A^1$ has the meaning of $A^2$, and $A^{1'}$ has the meaning of $A^{2'}$.

In a preferred embodiment the present invention is directed to compounds of formula (Ia)

wherein $A^1$ and $A^{1'}$ are independently of each other a group of formula wherein $R^{116}$, $R^{117}$ and $R^{117'}$ are independently of each other H, or $C_1$-$C_{18}$alkyl; or $A^1$ and $A^{1'}$ together with the nitrogen atom to which they are bonded form a group of formula $R^8$ is a group of formula and
$R^9$ is a group of formula wherein
$R^{128}$, $R^{129}$, $R^{139}$ and $R^{131}$ are independently of each other H, $C_1$-$C_{18}$alkyl, $C_1$-$C_{18}$alkoxy, or $C_1$-$C_{18}$perfluoroalkyl. In said embodiment $A^1$ and $A^{1'}$ are preferably independently of each other a group of formula and $R^9$ is
preferably a group of formula In another preferred embodiment the present invention is directed to compounds of formula (Ia)

wherein A¹ and A¹' are independently of each other a group of formula

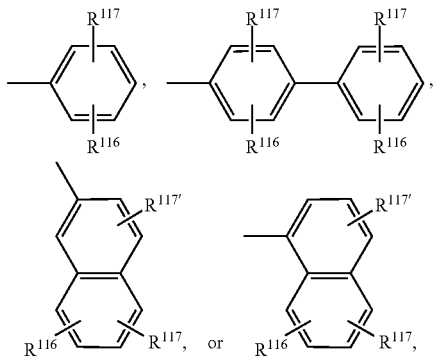

or A¹ and A¹' together with the nitrogen atom to which they are bonded form a group of formula

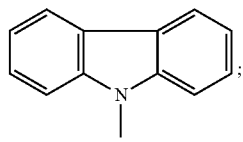

wherein $R^{116}$, $R^{117}$ and $R^{117'}$ are independently of each other H, or $C_1$-$C_{18}$alkyl:
$R^8$ is a group of formula

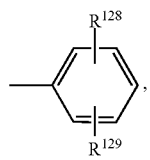

and
$R^9$ is a group of formula

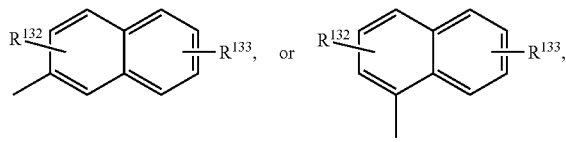

wherein
$R^{128}$, $R^{129}$, $R^{132}$ and $R^{133}$ are independently of each other H, $C_1$-$C_{18}$alkyl, $C_1$-$C_{18}$alkoxy, or $C_1$-$C_{18}$perfluoroalkyl. In said embodiment A¹ and A¹' are preferably independently of each other a group of formula

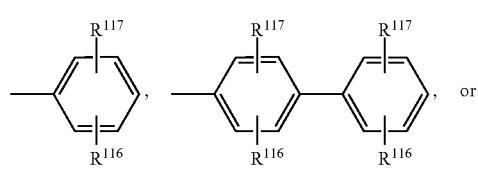

-continued

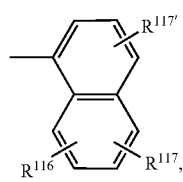

and $R^9$ is preferably a group of formula

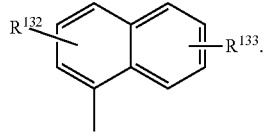

Examples of particularly preferred compounds are compounds A-1 to A-45 shown in claim 10. At present, compounds of formula

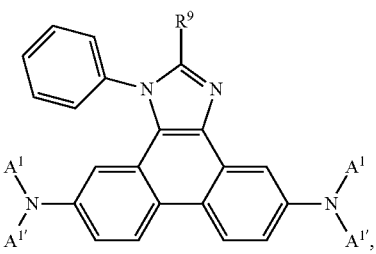

such as, for example, compounds A-1, A-5, A-7, A-11, A-31 and A-35, are most preferred, wherein A¹ and A¹' are independently of each other

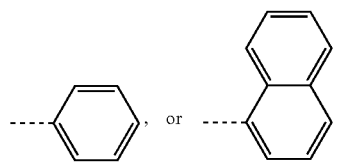

and $R^9$ is

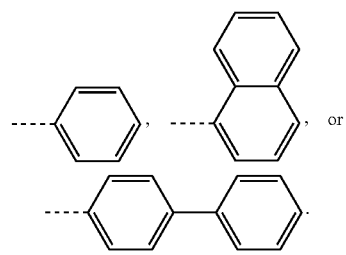

The compounds of the formula I, can, for example, be prepared according to a process, which comprises reacting a compound of formula

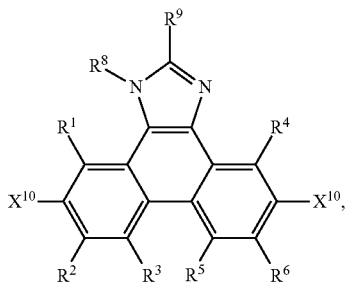

(II)

wherein $X^{10}$ stands for halogen, such as bromo or iodo, preferably iodo, with a compound of formula $HNA^1A^{1'}$, or

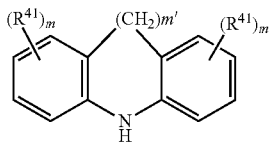

in the presence of a base, such as sodium hydride, potassium carbonate, or sodium carbonate, and a catalyst, such as copper (0) or copper (I) (such as copper, copper-bronze, copper bromide iodide, or copper bromide) in a solvent, such as toluene, dimethyl formamide, or dimethyl sulfoxide, wherein m', $A^1$, $A^{1'}$, $R^1$, $R^2$, $R^3$, $R^4$, $R^5$, $R^6$, $R^8$, $R^9$, $R^{41}$ and m are as defined above (WO08/031743). This reaction, referred to as an Ullmann condensation, is described by Yamamoto & Kurata, Chem. and Industry, 737-738 (1981), J. Mater. Chem. 14 (2004) 2516, H. B. Goodbrand et al., J. Org. Chem. 64 (1999) 670 and k. D. Belfield et al., J. Org. Chem. 65 (2000) 4475 using copper as catalyst. Additionally palladium catalysts can be used for the coupling of aryl halogen compounds with amines, as described in M. D. Charles et al., Organic Lett. 7 (2005) 3965, A. F. Littke et. al., Angew. Chem. Int. Ed. 41 (2002) 4176 and literature cited therein.

The compounds of formula II are known from WO06/097419, or WO08/031743, or can be prepared according, or in analogy to the methods described therein.

Halogen is fluorine, chlorine, bromine and iodine.

$C_1$-$C_{18}$alkyl is typically linear or branched, where possible. Examples are methyl, ethyl, n-propyl, isopropyl, n-butyl, sec.-butyl, isobutyl, tert.-butyl, n-pentyl, 2-pentyl, 3-pentyl, 2,2-dimethylpropyl, 1,1,3,3-tetramethylpentyl, n-hexyl, 1-methylhexyl, 1,1,3,3,5,5-hexamethylhexyl, n-heptyl, isoheptyl, 1,1,3,3-tetramethylbutyl, 1-methylheptyl, 3-methylheptyl, n-octyl, 1,1,3,3-tetramethylbutyl and 2-ethylhexyl, n-nonyl, decyl, undecyl, dodecyl, tridecyl, tetradecyl, pentadecyl, hexadecyl, heptadecyl, or octadecyl. $C_1$-$C_8$alkyl is typically methyl, ethyl, n-propyl, isopropyl, n-butyl, sec.-butyl, isobutyl, tert.-butyl, n-pentyl, 2-pentyl, 3-pentyl, 2,2-dimethyl-propyl, n-hexyl, n-heptyl, n-octyl, 1,1,3,3-tetramethylbutyl and 2-ethylhexyl. $C_1$-$C_4$alkyl is typically methyl, ethyl, n-propyl, isopropyl, n-butyl, sec.-butyl, isobutyl, tert.-butyl.

$C_1$-$C_{18}$alkoxy groups are straight-chain or branched alkoxy groups, e.g. methoxy, ethoxy, n-propoxy, isopropoxy, n-butoxy, sec-butoxy, tert-butoxy, amyloxy, isoamyloxy or tert-amyloxy, heptyloxy, octyloxy, isooctyloxy, nonyloxy, decyloxy, undecyloxy, dodecyloxy, tetradecyloxy, pentadecyloxy, hexadecyloxy, heptadecyloxy and octadecyloxy. Examples of $C_1$-$C_8$alkoxy are methoxy, ethoxy, n-propoxy, isopropoxy, n-butoxy, sec.-butoxy, isobutoxy, tert.-butoxy, n-pentyloxy, 2-pentyloxy, 3-pentyloxy, 2,2-dimethylpropoxy, n-hexyloxy, n-heptyloxy, n-octyloxy, 1,1,3,3-tetramethylbutoxy and 2-ethylhexyloxy, preferably $C_1$-$C_4$alkoxy such as typically methoxy, ethoxy, n-propoxy, isopropoxy, n-butoxy, sec.-butoxy, isobutoxy, tert.-butoxy. The term "alkylthio group" means the same groups as the alkoxy groups, except that the oxygen atom of the ether linkage is replaced by a sulfur atom.

$C_2$-$C_{18}$alkenyl groups are straight-chain or branched alkenyl groups, such as e.g. vinyl, allyl, methallyl, isopropenyl, 2-butenyl, 3-butenyl, isobutenyl, n-penta-2,4-dienyl, 3-methyl-but-2-enyl, n-oct-2-enyl, n-dodec-2-enyl, isododecenyl, n-dodec-2-enyl or n-octadec-4-enyl.

$C_{2-18}$alkynyl is straight-chain or branched and preferably $C_{2-8}$alkynyl, which may be unsubstituted or substituted, such as, for example, ethynyl, 1-propyn-3-yl, 1-butyn-4-yl, 1-pentyn-5-yl, 2-methyl-3-butyn-2-yl, 1,4-pentadiyn-3-yl, 1,3-pentadiyn-5-yl, 1-hexyn-6-yl, cis-3-methyl-2-penten-4-yn-1-yl, trans-3-methyl-2-penten-4-yn-1-yl, 1,3-hexadiyn-5-yl, 1-octyn-8-yl, 1-nonyn-9-yl, 1-decyn-10-yl, or 1-tetracosyn-24-yl.

$C_1$-$C_{18}$perfluoroalkyl, especially $C_1$-$C_4$perfluoroalkyl, is a branched or unbranched radical such as for example —$CF_3$, —$CF_2CF_3$, —$CF_2CF_2CF_3$, —$CF(CF_3)_2$, —$(CF_2)_3CF_3$, and —$C(CF_3)_3$.

The term "cycloalkyl group" is typically $C_4$-$C_{18}$cycloalkyl, such as cyclopentyl, cyclohexyl, cycloheptyl, cyclooctyl, cyclononyl, cyclodecyl, cycloundecyl, cyclododecyl, preferably cyclopentyl, cyclohexyl, cycloheptyl, or cyclooctyl, which may be unsubstituted or substituted. The term "cycloalkenyl group" means an unsaturated alicyclic hydrocarbon group containing one or more double bonds, such as cyclopentenyl, cyclopentadienyl, cyclohexenyl and the like, which may be unsubstituted or substituted. The cycloalkyl group, in particular a cyclohexyl group, can be condensed one or two times by phenyl which can be substituted one to three times with $C_1$-$C_4$-alkyl, halogen and cyano. Examples of such condensed cyclohexyl groups are:

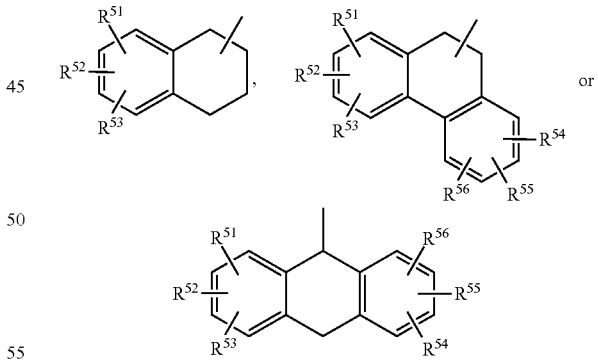

in particular

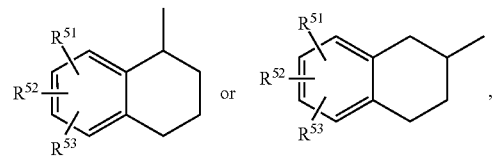

wherein $R^{51}$, $R^{52}$, $R^{53}$, $R^{54}$, $R^{55}$ and $R^{56}$ are independently of each other $C_1$-$C_8$-alkyl, $C_1$-$C_8$-alkoxy, halogen and cyano, in particular hydrogen.

Aryl is usually $C_6$-$C_{24}$aryl ($C_6$-$C_{18}$aryl), which optionally can be substituted, such as, for example, phenyl, 4-methylphenyl, 4-methoxyphenyl, naphthyl, especially 1-naphthyl, or 2-naphthyl, biphenylyl, terphenylyl, pyrenyl, 2- or 9-fluorenyl, phenanthryl, anthryl, tetracyl, pentacyl, hexacyl, or quaderphenylyl, which may be unsubstituted or substituted.

The term "aralkyl group" is typically $C_7$-$C_{25}$aralkyl, such as benzyl, 2-benzyl-2-propyl, (3-phenyl-ethyl, α,α-dimethylbenzyl, ω-phenyl-butyl, ω,ω-dimethyl-ω-phenyl-butyl, ω-phenyl-dodecyl, ω-phenyl-octadecyl, ω-phenyl-eicosyl or ω-phenyl-docosyl, preferably $C_7$-$C_{18}$aralkyl such as benzyl, 2-benzyl-2-propyl, 3-phenyl-ethyl, α,α-dimethylbenzyl, ω-phenyl-butyl, ω,ω-dimethyl-ω-phenyl-butyl, ω-phenyl-dodecyl or ω-phenyl-octadecyl, and particularly preferred $C_7$-$C_{12}$aralkyl such as benzyl, 2-benzyl-2-propyl, 3-phenyl-ethyl, α,α-dimethylbenzyl, ω-phenyl-butyl, or ω,ω-dimethyl-ω-phenyl-butyl, in which both the aliphatic hydrocarbon group and aromatic hydrocarbon group may be unsubstituted or substituted.

Heteroaryl is typically $C_2$-$C_{20}$heteroaryl, i.e. a ring with five to seven ring atoms or a condensed ring system, wherein nitrogen, oxygen or sulfur are the possible hetero atoms, and is typically an unsaturated heterocyclic group with five to 30 atoms having at least six conjugated π-electrons such as thienyl, benzo[b]thienyl, dibenzo[b,d]thienyl, thianthrenyl, furyl, furfuryl, 2H-pyranyl, benzofuranyl, isobenzofuranyl, dibenzofuranyl, phenoxythienyl, pyrrolyl, imidazolyl, pyrazolyl, pyridyl, bipyridyl, triazinyl, pyrimidinyl, pyrazinyl, pyridazinyl, indolizinyl, isoindolyl, indolyl, indazolyl, purinyl, quinolizinyl, chinolyl, isochinolyl, phthalazinyl, naphthyridinyl, chinoxalinyl, chinazolinyl, cinnolinyl, pteridinyl, carbazolyl, carbolinyl, benzotriazolyl, benzoxazolyl, phenanthridinyl, acridinyl, pyrimidinyl, phenanthrolinyl, phenazinyl, isothiazolyl, phenothiazinyl, isoxazolyl, furazanyl or phenoxazinyl, which can be unsubstituted or substituted.

Possible substituents of the above-mentioned groups are $C_1$-$C_8$alkyl, a hydroxyl group, a mercapto group, $C_1$-$C_8$alkoxy, $C_1$-$C_8$alkylthio, halogen, halo-$C_1$-$C_8$alkyl, a cyano group, an aldehyde group, a ketone group, a carboxyl group, an ester group, a carbamoyl group, an amino group, a nitro group or a silyl group. Preferred substituents of the above-mentioned groups are $C_1$-$C_8$alkyl, $C_1$-$C_8$alkoxy, $C_1$-$C_8$alkylthio, and a cyano group, If a substituent, such as, for example $R^{41}$ occurs more than one time in a group, it can be different in each occurrence.

The wording "substituted by G" means that one, or more, especially one to three substituents G might be present.

As described above, the aforementioned groups may be substituted by E and/or, if desired, interrupted by D. Interruptions are of course possible only in the case of groups containing at least 2 carbon atoms connected to one another by single bonds; $C_6$-$C_{24}$aryl is not interrupted; interrupted arylalkyl or alkylaryl contains the unit D in the alkyl moiety. $C_1$-$C_{18}$alkyl substituted by one or more E and/or interrupted by one or more units D is, for example, $(CH_2CH_2O)_{1-9}$—$R^x$, where $R^x$ is H or $C_1$-$C_{10}$alkyl or $C_2$-$C_{10}$alkanoyl (e.g. CO—CH($C_2H_5$)$C_4H_9$), $CH_2$—CH($OR^y$)—$CH_2$—O—$R^y$, where $R^y$ is $C_1$-$C_{18}$alkyl, $C_5$-$C_{12}$cycloalkyl, phenyl, $C_7$-$C_{15}$-phenylalkyl, and $R^{y'}$ embraces the same definitions as $R^y$ or is H;

$C_1$-$C_8$alkylene-COO—$R^z$, e.g. $CH_2COOR^z$, $CH(CH_3)CO$-$OR^z$, $C(CH_3)_2COOR^z$, where $R^z$ is H, $C_1$-$C_{18}$alkyl, $(CH_2CH_2O)_{1-9}$—$R^x$, and $R^x$ embraces the definitions indicated above; $CH_2CH_2$—O—CO—CH=$CH_2$; $CH_2CH(OH)$ $CH_2$—O—CO—C($CH_3$)=$CH_2$.

General Device Architecture

The compounds of formula I can be employed in many OLED device configurations using small molecule materials, oligomeric materials, polymeric materials, or combinations thereof. These include very simple structures comprising a single anode and cathode to more complex devices, such as passive matrix displays comprised of orthogonal arrays of anodes and cathodes to form pixels, and active-matrix displays where each pixel is controlled independently, for example, with thin film transistors (TFTs).

The organic light-emitting device of the present invention has a pair of electrodes composed of an anode and a cathode, and layers each containing an organic compound including at least a light-emitting layer and a hole-transporting/injecting layer, disposed between the pair of electrodes.

A first constitution comprises sequentially on the substrate, the anode, the hole-transporting/injecting layer, the light-emitting layer, the electron-transporting layer, and the cathode. In this constitution, a carrier-transporting function and a light-emitting function are separated from each other, and a region in which holes and electrons recombine is present in the light-emitting layer.

A second constitution differs from the above first constitution in that the hole-transporting/injecting layer comprises a hole injecting layer and a hole-transporting layer. The layer has an improving effect on hole injection property, and is effective for reducing the drive voltage.

A third constitution differs from the above first constitution in that a layer (hole-blocking layer) for inhibiting holes from penetrating toward the cathode side is further provided between the light-emitting layer and the electron-transporting layer. The constitution is effective for an improvement in emission efficiency when a compound having a large ionization potential (that is, a deep HOMO) is used in the hole-blocking layer.

The compounds of formula I can be employed as a component of the hole transport/injecting layer. It is preferable that the compounds of formula I as a main component of the hole-transporting layer facilitates injection of holes from an anode and has an excellent mobility for transporting the injected holes to a light-emitting layer.

Alternatively, the compounds of formula I can be employed as a component of the electron blocking layer.

A typical structure, especially useful for of a small molecule device, is comprised of a substrate, an anode, a hole transporting/injecting layer, optionally an electron blocking layer, a light-emitting layer, optionally a hole- or exciton-blocking layer, an electron-transporting layer, and a cathode. A preferred structure, especially useful for of a small molecule device, is comprised of a substrate, an anode, a hole transporting/injecting layer, an electron blocking layer, a light-emitting layer, a hole-blocking layer, an electron-transporting layer, and a cathode.

These layers are described in detail below. Note that the substrate may alternatively be located adjacent to the cathode, or the substrate may actually constitute the anode or cathode. The organic layers between the anode and cathode are conveniently referred to as the organic EL element. Also, the total combined thickness of the organic layers is desirably less than 500 nm.

Host Materials for Phosphorescent Materials

The compounds of formula I can also be used in organic light emitting diodes (OLEDs) as hosts for phosphorescent compounds. Reference is made to WO08/031743.

Suitably, the light-emitting layer of the OLED device comprises a host material and one or more guest materials for emitting light. The light-emitting guest material(s) is usually present in an amount less than the amount of host materials and is typically present in an amount of up to 15 wt % of the host, more typically from 0.1 to 10 wt % of the host, and commonly from 5 to 10% of the host. For convenience, the phosphorescent complex guest material may be referred to herein as a phosphorescent material. The emissive layer may comprise a single material, that combines transport and emissive properties. Whether the emissive material is a dopant or a major constituent, emissive layer may comprise other materials, such as dopants that tune the emission of the emissive layer. The emissive layer may include a plurality of emissive materials capable of, in combination, emitting a desired spectrum of light.

The host material useful in the invention may be used alone or in combination with other host materials. The host materials should be selected so that the triplet exciton can be transferred efficiently from the host material to the phosphorescent material. Suitable host materials are described in WO00/70655; WO01/39234; WO01/93642; WO02/074015; WO02/15645, US20020117662 and WO08/031743. Suitable hosts include certain aryl amines, triazoles, indoles and carbazole compounds. Examples of hosts are 4,4'-bis[N-(1-naphtyl)-N-phenylamino]biphenyl (α-NPD), 4,4'-N,N'-dicarbazole-biphenyl (CBP), 2,2'-dimethyl-4,4'-N,N'-dicarbazole-biphenyl, m-(N,N'-dicarbazole)benzene, and poly(N-vinylcarbazole), including their derivatives.

Desirable host materials are capable of forming a continuous film. The light-emitting layer may contain more than one host material in order to improve the device's film morphology, electrical properties, light emission efficiency, and lifetime. The light emitting layer may contain a first host material that has good hole-transporting properties, and a second host material that has good electron-transporting properties.

Phosphorescent Materials

Phosphorescent materials may be used alone or, in certain cases, in combination with each other, either in the same or different layers. Examples of phosphorescent and related materials are described in WO00/57676, WO00/70655, WO01/41512, WO02/15645, US2003/0017361, WO01/93642, WO01/39234, U.S. Pat. No. 6,458,475, WO02/071813, U.S. Pat. No. 6,573,651, US2002/0197511, WO02/074015, U.S. Pat. No. 6,451,455, US2003/0072964, US2003/0068528, U.S. Pat. Nos. 6,413,656, 6,515,298, 6,451,415, 6,097,147, US2003/0124381, US2003/0059646, US2003/0054198, EP1239526, EP1238981, EP1244155, US2002/0100906, US2003/0068526, US2003/0068535, JP2003073387, JP2003073388, US2003/0141809, US2003/0040627, JP2003059667, JP2003073665 and US2002/0121638.

The emission wavelengths of cyclometallated Ir(III) complexes of the type $IrL_3$ and $IrL_2L'$, such as the green-emitting fac-tris(2-phenylpyridinato-$N,C^{2'}$)iridium(III) and bis(2-phenylpyridinato-$N,C^{7}$)Iridium(III) (acetylacetonate) may be shifted by substitution of electron donating or withdrawing groups at appropriate positions on the cyclometallating ligand L, or by choice of different heterocycles for the cyclometallating ligand L. The emission wavelengths may also be shifted by choice of the ancillary ligand L'. Examples of red emitters are the bis(2-(2'-benzothienyl)pyridinato-$N,C^3$)iridium(III)(acetylacetonate), iridium(III)bis(2-methyldibenzo[f,h]quinoxaline) (acetylacetonate), and tris(1-phenylisoquinolinato-N,C)iridium(III). A blue-emitting example is bis (2-(4,6-difluorophenyl)-pyridinato-$N,C^{2'}$)Iridium(III) (picolinate).

Red electrophosphorescence has been reported, using bis (2-(2'-benzo[4,5-a]thienyl)pyridinato-$N,C^3$)iridium(acetylacetonate)[$Btp_2Ir(acac)$] as the phosphorescent material (Adachi, C., Lamansky, S., Baldo, M. A., Kwong, R. C., Thompson, M. E., and Forrest, S. R., App. Phys. Lett., 78, 1622 1624 (2001).

Other important phosphorescent materials include cyclometallated Pt(II) complexes such as cis-bis(2-phenylpyridinato-$N,C^{2'}$)platinum(II), cis-bis(2-(2'-thienyl)pyridinato-N, $C^3$) platinum(II), cis-bis(2-(2'-thienyl)quinolinato-$N,C^{5'}$) platinum(II), or (2-(4,6-difluorophenyl)pyridinato-NC2') platinum(II)acetylacetonate. Pt(II)porphyrin complexes such as 2,3,7,8,12,13,17,18-octaethyl-21H,23H-porphine platinum(H) are also useful phosphorescent materials.

Still other examples of useful phosphorescent materials include coordination complexes of the trivalent lanthanides such as $Th^{3+}$ and $Eu^{3+}$ (J. Kido et al, Appl. Phys. Lett., 65, 2124 (1994)).

Other important phosphorescent materials are described in WO06/000544 and WO08/101842.

Blocking Layers

In addition to suitable hosts, an OLED device employing a phosphorescent material often requires at least one exciton or hole blocking layer to help confine the excitons or electron-hole recombination centers to the light-emitting layer comprising the host and phosphorescent material, or to reduce the number of charge carriers (electrons or holes). In one embodiment, such a blocking layer would be placed between the electron-transporting layer and the light-emitting layer. In this case, the ionization potential of the blocking layer should be such that there is an energy barrier for hole migration from the host into the electron-transporting layer, while the electron affinity should be such that electrons pass more readily from the electron-transporting layer into the light-emitting layer comprising host and phosphorescent material. It is further desired, but not absolutely required, that the triplet energy of the blocking material be greater than that of the phosphorescent material. Suitable hole-blocking materials are described in WO00/70655 and WO01/93642. Two examples of useful materials are bathocuproine (BCP) and bis(2-methyl-8-quinolinolato)(4-phenylphenolato)aluminum(III) (BAlq), which may be doped by, for example, caesium. Metal complexes other than Balq are also known to block holes and excitons as described in US20030068528. US20030175553 describes the use of fac-tris(1-phenylpyrazolato-N,C 2)iridium(III) (Irppz) in an electron/exciton blocking layer. Alternatively, 4,4'-bis[N-(1-naphtyl)-N-phenylamino]biphenyl (α-NPD) may be used in an electron/exciton blocking layer.

Alternatively, the compounds of formula I can be used as material for the electron blocking layer. The compounds of formula I may function alone, to provide improved efficiency, driving voltage and/or lifetime of electroluminescent devices.

Substrate

The substrate can either be light transmissive or opaque, depending on the intended direction of light emission. The light transmissive property is desirable for viewing the EL emission through the substrate. Transparent glass or plastic is commonly employed in such cases. The substrate can be a complex structure comprising multiple layers of materials. This is typically the case for active matrix substrates wherein TFTs are provided below the OLED layers. It is still necessary that the substrate, at least in the emissive pixilated areas, be comprised of largely transparent materials such as glass or polymers. For applications where the EL emission is viewed through the top electrode, the transmissive characteristic of the bottom support is immaterial, and therefore can be light transmissive, light absorbing or light reflective. Substrates for use in this case include, but are not limited to, glass, plastic, semiconductor materials, silicon, ceramics, and circuit board materials. Again, the substrate can be a complex structure comprising multiple layers of materials such as found in active matrix TFT designs. It is necessary to provide in these device configurations a light-transparent top electrode.

Anode

When the desired electroluminescent light emission (EL) is viewed through the anode, the anode should be transparent or substantially transparent to the emission of interest. Common transparent anode materials used in this invention are indium-tin oxide (ITO), indium-zinc oxide (IZO) and tin oxide, but other metal oxides can work including, but not limited to, aluminum- or indium-doped zinc oxide, magnesium-indium oxide, and nickel-tungsten oxide. In addition to these oxides, metal nitrides, such as gallium nitride, and metal selenides, such as zinc selenide, and metal sulfides, such as zinc sulfide, can be used as the anode. For applications where EL emission is viewed only through the cathode, the transmissive characteristics of the anode are immaterial and any conductive material can be used, transparent, opaque or reflective. Example conductors for this application include, but are not limited to, gold, iridium, molybdenum, palladium, and platinum. Desired anode materials are commonly deposited by any suitable means such as evaporation, sputtering, chemical vapor deposition, or electrochemical means. Anodes can be patterned using well-known photolithographic processes. Optionally, anodes may be polished prior to application of other layers to reduce surface roughness so as to minimize shorts or enhance reflectivity.

Cathode

When light emission is viewed solely through the anode, the cathode used in this invention can be comprised of nearly any conductive material. Desirable materials have good film-forming properties to ensure good contact with the underlying organic layer, promote electron injection at low voltage, and have good stability. Useful cathode materials often contain a low work function metal (<4.0 eV) or metal alloy. One useful cathode material is comprised of a Mg:Ag alloy wherein the percentage of silver is in the range of 1 to 20%, as described in U.S. Pat. No. 4,885,221. Another suitable class of cathode materials includes bilayers comprising the cathode and a thin electron-injection layer (EIL) in contact with an organic layer (e.g., an electron transporting layer (ETL)) which is capped with a thicker layer of a conductive metal. Here, the EIL preferably includes a low work function metal or metal salt, and if so, the thicker capping layer does not need to have a low work function. One such cathode is comprised of a thin layer of LiF followed by a thicker layer of Al as described in U.S. Pat. No. 5,677,572. An ETL material doped with an alkali metal, for example, Li-doped Alq, is another example of a useful EIL. Other useful cathode material sets include, but are not limited to, those disclosed in U.S. Pat. Nos. 5,059,861, 5,059,862 and 6,140,763.

When light emission is viewed through the cathode, the cathode must be transparent or nearly transparent. For such applications, metals must be thin or one must use transparent conductive oxides, or a combination of these materials. Optically transparent cathodes have been described in more detail in U.S. Pat. Nos. 4,885,211, 5,247,190, JP 3,234,963, U.S. Pat. Nos. 5,703,436, 5,608,287, 5,837,391, 5,677,572, 5,776,622, 5,776,623, 5,714,838, 5,969,474, 5,739,545, 5,981,306, 6,137,223, 6,140,763, 6,172,459, EP1076368, U.S. Pat. Nos. 6,278,236 and 6,284,3936. Cathode materials are typically deposited by any suitable method such as evaporation, sputtering, or chemical vapor deposition. When needed, patterning can be achieved through many well known methods including, but not limited to, through-mask deposition, integral shadow masking as described in U.S. Pat. No. 5,276,380 and EP0732868, laser ablation, and selective chemical vapor deposition.

Hole Transporting/Injecting Layer (HTL)

The hole transporting/injecting layer is not limited to a single layer, and two, or more layers, in which at least one layer is made of a compound of formula I may be stacked. If the hole transporting/injecting layer consists of two, or more layers (hole injecting layer/hole trans-port layer), the compound of formula I is contained in the layer next to the anode (hole injecting layer). The hole transporting/injecting layer of the organic EL device contains at least one compound of formula I. The hole transporting/injecting layer can be formed of a single compound of formula I, or a mixture of compounds of formula I, or a mixture of compounds of formula I with other compounds (so-called "dopants"). hole transporting/injecting layer is preferably a single layer, comprising a compound of formula I and a dopant. The dopant(s) is used in an amount 0.001 to 20% by weight, especially 1 to 20% by weight based on the weight of compound of formula I and dopant. Examples of dopants are, for example, mentioned in K. Walzer, B. Maennig, M. Pfeiffer, and K. Leo, Chem. Rev. 107 (2007) 1233-1271, EP1596445A1, WO2009/003455A1, DE100357044, WO2008/058525, WO2008/138580, US20080171228 and US2008/0265216. Specific examples of dopants, which can used in combination of compounds of formula I are: titanium oxide (TiO$_x$), vanadium oxide (VO$_x$), especially V$_2$O$_5$, molybdenium oxide (MoOx), especially MoO$_3$, tungsten oxide (WO$_x$), especially WO$_3$, ruthenium oxide (RuO$_x$), chromium oxide (CrO$_x$), zirconium oxide (ZrO$_x$), hafnium oxide (HfO$_x$) tantalum oxide (TaO$_x$) silver oxide (AgO$_x$), manganese oxide (MnO$_x$), iron trichloride (FeCl$_3$), antimony pentachloride (SbCl$_5$), metal phthalocyanine compounds as described in WO2008/058525, dicyano(phthalocyanato(−1)cobalt(III), the oxocarbon-, pseudooxocarbon- and radialene compounds described in US2008/0265216, dicyano(phthalocyanato(−1)ruthenium (III) as described in WO2008/138580, especially MO$_3$, 2-(6-dicyanomethylene-1,3,4,5,7,8-hexafluoro-6H-naphthalen-2-ylidene)-malononitrile,

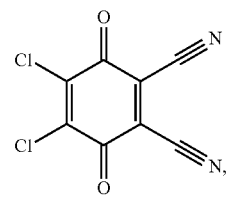

-continued

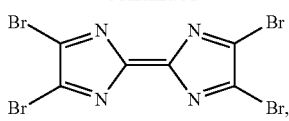

2,3,5,6-tetrafluoro-7,7,8,8-tetracyanoquinodimethane (F4-TCNQ),

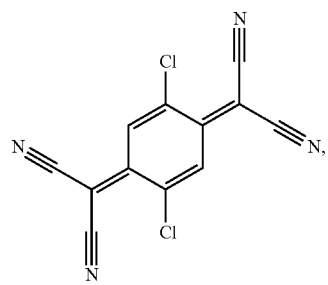

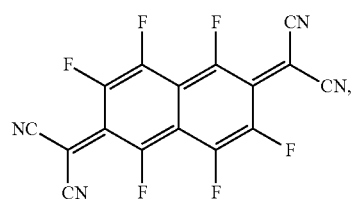

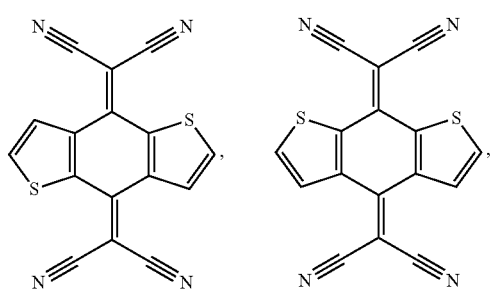

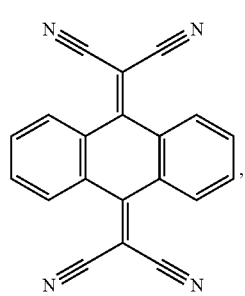

-continued

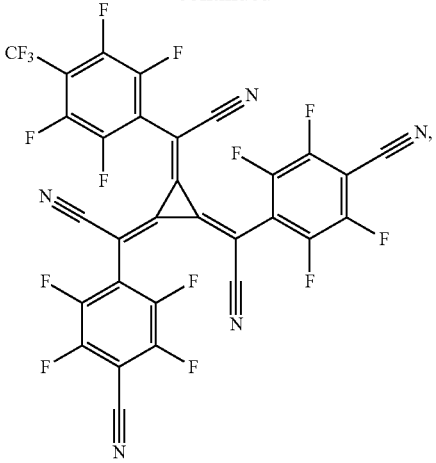

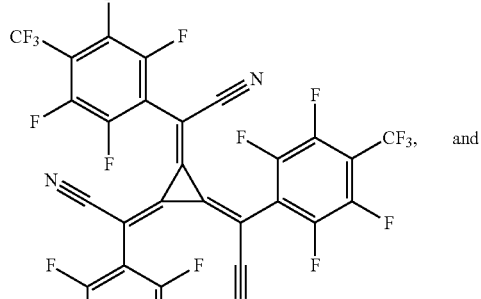 and

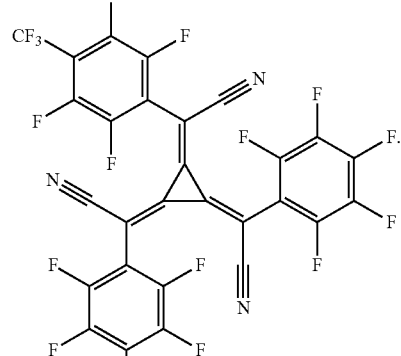

Specifically, one may employ especially $MoO_3$ as dopant of the hole transporting/injecting layer in an amount of 1 to 20% by weight based on the weight of compound of formula I and dopant. Alternatively, one can employ a mixture of compounds of formula I with 2,3,5,6-tetrafluoro-7,7,8,8-tetracyanoquinodimethane (F4-TCNQ) as dopant in an amount 1 to 20% by weight based on the weight of compound of formula I and dopant.

Doping of the respective compound of formula I (matrix material) with the dopants to be used according to the present invention may be produced by one or a combination of the following methods: a) mixed evaporation under vacuum with one source for the matrix material and one for the dopant; b) sequential deposition of the matrix material and dopant with subsequent in-diffusion of the dopant by heat treatment; c)

doping of a matrix material layer by a solution of dopant with subsequent evaporation of the solvent by heat treatment; and d) superficial doping of a matrix material layer by a layer of dopant applied to the surface.

Alternative materials for use in the hole-injecting layer include porphyrinic compounds as described in U.S. Pat. No. 4,720,432, plasma-deposited fluorocarbon polymers as described in U.S. Pat. No. 6,208,075, and some aromatic amines, for example, m-MTDATA (4,4',4"-tris[(3-methylphenyl)phenylamino]triphenylamine). Alternative hole-injecting materials reportedly useful in organic EL devices are described in EP0891121 and EP1029909.

As an alternative substance for the hole transporting layer the following aromatic amine compounds can be used for example: 4,4'-bis[N-(1-napthyl)-N-phenylamino]biphenyl (abbreviation: NPB); N,N'-bis(3-methylphenyl)-N,N'-dipheny-[1,1'-biphenyl]-4,4'-diamine (abbreviation TPD); 4,4',4"-tris(N,N-diphenylamino)triphenylamine (abbreviation TDATA); 4,4',4"-tris[N-(3-methylphenyl)-N-phenylamino]triphenylamine (abbreviation MTDATA); and 4,4'-bis[N-(spiro-9,9'-bifluoren-2-yl)-N-phenylamino]biphenyl (abbreviation: BSPB).

Fluorescent Light-Emitting Materials and Layers (LEL)

In addition to the phosphorescent materials, other light emitting materials may be used in the OLED device, including fluorescent materials. Although the term "fluorescent" is commonly used to describe any light emitting material, in this case we are referring to a material that emits light from a singlet excited state. Fluorescent materials may be used in the same layer as the phosphorescent material, in adjacent layers, in adjacent pixels, or any combination. Care must be taken not to select materials that will adversely affect the performance of the phosphorescent materials. One skilled in the art will understand that triplet excited state energies of materials in the same layer as the phosphorescent material or in an adjacent layer must be appropriately set so as to prevent unwanted quenching. As more fully described in U.S. Pat. Nos. 4,769, 292 and 5,935,721, the light-emitting layer (LEL) of the organic EL element includes a luminescent fluorescent or phosphorescent material where electroluminescence is produced as a result of electron-hole pair recombination in this region. The light-emitting layer can be comprised of a single material, but more commonly consists of a host material doped with a guest emitting material or materials where light emission comes primarily from the emitting materials and can be of any color. The host materials in the light-emitting layer can be an electron-transporting material, as defined below, a hole-transporting material, as defined above, or another material or combination of materials that support hole-electron recombination. Fluorescent emitting materials are typically incorporated at 0.01 to 10% by weight of the host material. The host and emitting materials can be small non-polymeric molecules or polymeric materials such as polyfluorenes and polyvinylarylenes (e.g., poly(p-phenylenevinylene), PPV). In the case of polymers, small molecule emitting materials can be molecularly dispersed into a polymeric host, or the emitting materials can be added by copolymerizing a minor constituent into a host polymer. Host materials may be mixed together in order to improve film formation, electrical properties, light emission efficiency, lifetime, or manufacturability. The host may comprise a material that has good hole-transporting properties and a material that has good electron-transporting properties.

Host and emitting materials known to be of use include, but are not limited to, those disclosed in U.S. Pat. Nos. 4,768,292, 5,141,671, 5,150,006, 5,151,629, 5,405,709, 5,484,922, 5,593,788, 5,645,948, 5,683,823, 5,755,999, 5,928,802, 5,935,720, 5,935,721, and 6,020,078.

Metal complexes of 8-hydroxyquinoline and similar derivatives (Formula E) constitute one class of useful host compounds capable of supporting electroluminescence, and are particularly suitable for light emission of wavelengths longer than 500 nm, e.g., green, yellow, orange, and red.

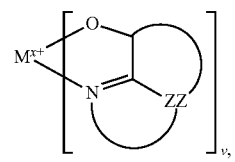

wherein M represents a metal; v is an integer of from 1 to 4; and ZZ independently in each occurrence represents the atoms completing a nucleus having at least two fused aromatic rings. From the foregoing it is apparent that the metal can be monovalent, divalent, trivalent, or tetravalent metal. The metal can, for example, be an alkali metal, such as lithium, sodium, or potassium; an alkaline earth metal, such as magnesium or calcium; an earth metal, such aluminum or gallium, or a transition metal such as zinc or zirconium. Generally any monovalent, divalent, trivalent, or tetravalent metal known to be a useful chelating metal can be employed. ZZ completes a heterocyclic nucleus containing at least two fused aromatic rings, at least one of which is an azole or azine ring. Additional rings, including both aliphatic and aromatic rings, can be fused with the two required rings, if required. To avoid adding molecular bulk without improving on function the number of ring atoms is usually maintained at 18 or less.

Illustrative of useful chelated oxinoid compounds are the following:
CO-1: Aluminum trisoxine [alias, tris(8-quinolinolato)aluminum(III)]
CO-2: Magnesium bisoxine [alias, bis(8-quinolinolato)magnesium(II)]
CO-3: Bis[benzo{f}-8-quinolinolato]zinc(II)
CO-4: Bis(2-methyl-8-quinolinolato)aluminum(III)-μ-oxo-bis(2-methyl-8-quinol-inola-to)aluminum(III)
CO-5: Indium trisoxine [alias, tris(8-quinolinolato)indium]
CO-6: Aluminum tris(5-methyloxine) [alias, tris(5-methyl-8-quinolinolato) aluminum(III)]
CO-7: Lithium oxine [alias, (8-quinolinolato)lithium(I)]
CO-8: Gallium oxine [alias, tris(8-quinolinolato)gallium (III)]
CO-9: Zirconium oxine [alias, tetra(8-quinolinolato)zirconium(IV)]

Useful fluorescent emitting materials include, but are not limited to, derivatives of anthracene, tetracene, xanthene, perylene, rubrene, coumarin, rhodamine, and quinacridone, di-cyanomethylenepyran compounds, thiopyran compounds, polymethine compounds, pyrilium and thiapyrilium compounds, fluorene derivatives, periflanthene derivatives, indeno-perylene derivatives, bis(azinyl)amine boron compounds, bis(azinyl)methane compounds, and carbostyryl compounds. Illustrative examples of useful materials include, but are not limited to, compounds L1 to L52 described in U.S. Pat. No. 7,090,930B2.

Electron-Transporting Layer (ETL)

Preferred thin film-forming materials for use in forming the electron-transporting layer of the organic EL devices of this invention are metal chelated oxinoid compounds, including chelates of oxine itself (also commonly referred to as 8-quinolinol or 8-hydroxyquinoline). Such compounds help to inject and transport electrons and exhibit both high levels of performance and are readily fabricated in the form of thin films. Exemplary of contemplated oxinoid compounds are those satisfying structural formula (E), previously described. Other electron-transporting materials include various butadiene derivatives as disclosed in U.S. Pat. No. 4,356,429 and various heterocyclic optical brighteners as described in U.S. Pat. No. 4,539,507. Benzazoles satisfying structural formula (G) are also useful electron transporting materials. Triazines are also known to be useful as electron transporting materials. Doping may be used to enhance conductivity. Alq$_3$ is an example of an intrinsic electron transport layer. An example of an n-doped electron transport layer is BPhen doped with Li at a molar ratio of 1:1, as disclosed in U.S. Pat. No. 6,337,102.

Deposition of Organic Layers

The organic materials mentioned above are suitably deposited by any means suitable for the form of the organic materials. In the case of small molecules, they are conveniently deposited through thermal evaporation, but can be deposited by other means such as from a solvent with an optional binder to improve film formation. If the material is soluble or in oligomeric/polymeric form, solution processing is usually preferred e.g. spin-coating, ink-jet printing. Dendrimer substituents may be used to enhance the ability of small molecules to undergo solution processing. Patterned deposition can be achieved using shadow masks, integral shadow masks (U.S. Pat. No. 5,294,870), spatially-defined thermal dye transfer from a donor sheet (U.S. Pat. Nos. 5,688,551, 5,851, 709 and 6,066,357) and inkjet method (U.S. Pat. No. 6,066, 357).

Encapsulation

Most OLED devices are sensitive to moisture or oxygen, or both, so they are commonly sealed in an inert atmosphere such as nitrogen or argon, along with a desiccant such as alumina, bauxite, calcium sulfate, clays, silica gel, zeolites, alkaline metal oxides, alkaline earth metal oxides, sulfates, or metal halides and perchlorates. Methods for encapsulation and desiccation include, but are not limited to, those described in U.S. Pat. No. 6,226,890. In addition, barrier layers such as SiO$_x$, Teflon, and alternating inorganic/polymeric layers are known in the art for encapsulation.

Devices fabricated in accordance with embodiments of the invention may be incorporated into a wide variety of consumer products, including flat panel displays, computer monitors, televisions, billboards, lights for interior or exterior illumination and/or signalling, fully trans-parent displays, flexible displays, laser printers, cell phones, personal digital assistants (PDAs), laptop computers, digital cameras, camcorders, viewfinders, micro-displays, vehicles, theatre or stadium screen, or a sign. Various control mechanism may be used to control devices fabricated in accordance with the present invention, including passive matrix and active matrix.

Various features and aspects of the present invention are illustrated further in the examples that follow. While these examples are presented to show one skilled in the art how to operate within the scope of this invention, they are not to serve as a limitation on the scope of the invention where such scope is only defined in the claims. Unless otherwise indicated in the following examples and elsewhere in the specification and claims, all parts and percentages are by weight, temperatures are in degrees centigrade and pressures are at or near atmospheric.

EXAMPLES

Example 1

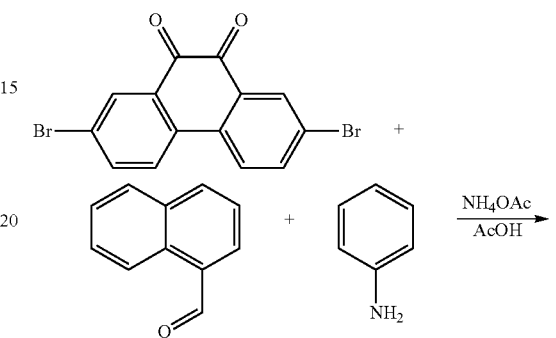

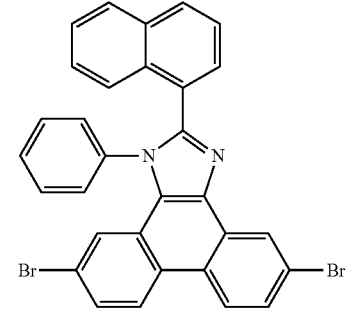

a) 30.0 g (82.0 mmol) 2,7-dibromo-phenanthrene-9,10-dione, 14.1 g (90.2 mmol) 1-naphthalene carboxaldehyde, 15.3 g (164 mmol) aniline and 19.0 g (246 mmol) ammonium acetate in 500 ml glacial acetic acid are refluxed for 4 h under nitrogen. The product is filtered off, washed with glacial acetic acid, water, a sodium hydrogen carbonate solution and water and then decocted in toluene and methyl ethyl ketone.

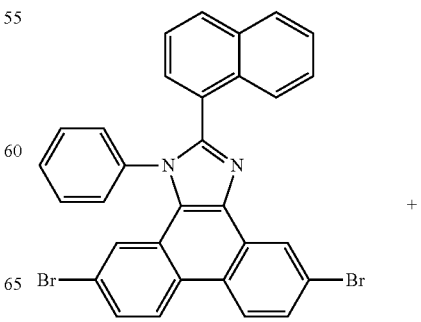

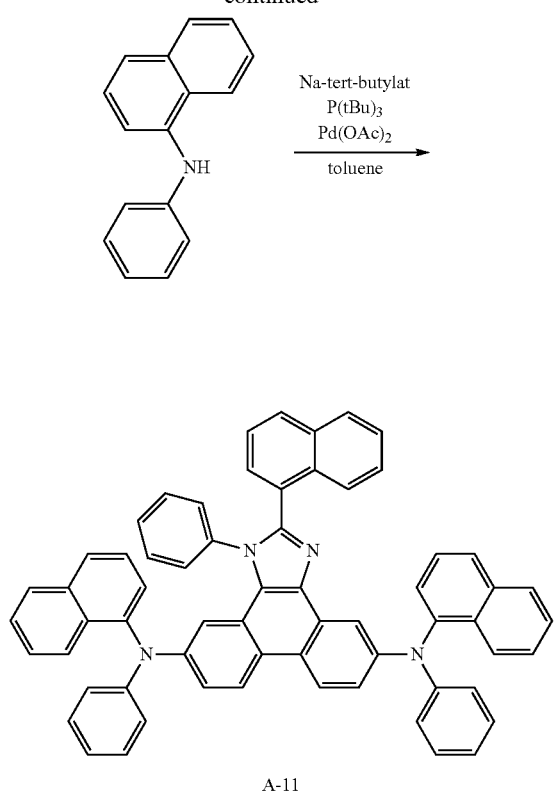

A-11

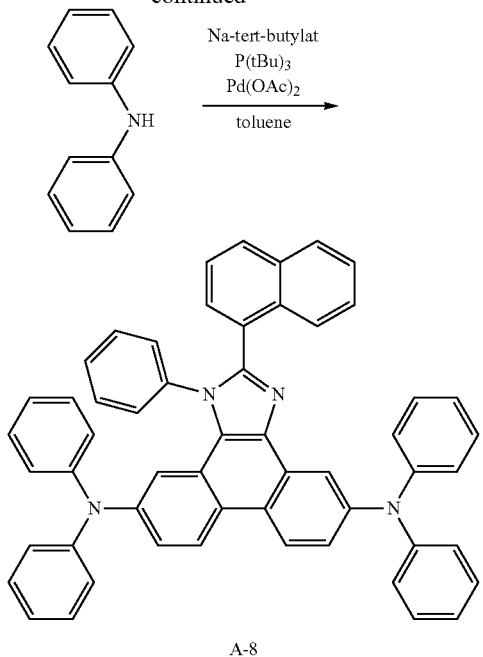

A-8

The synthesis is carried out in analogy to example 1b. The product has a melting point of 334° C.

$^1$H NMR (300 MHz, THF-d$_8$, ppm): δ=8.48 (d, J=9.2 Hz, 1H), 8.44 (d, J=9.1 Hz, 1H), 8.29 (d, J=2.4 Hz, 1H), 7.82-7.85 (m, 1H), 7.63-7.68 (m, 2H), 6.77-7.31 (m, 32H).

b) 3.66 g (38.0 mmol) sodium tert-butylate are added to 10.00 g (17.3 mmol) of the product of example 1a in 200 ml toluene. The reaction mixture is degassed with argon. 190 mg (0.86 mmol) palladium(II) acetate are added. The reaction mixture is degassed with argon. 350 mg (1.73 mmol) tri-tert-butylphosphine are added. A degassed solution of 7.96 g (36.3 mmol) N-phenyl-1-naphthylamine in 40 ml toluene is added. The reaction mixture is stirred for 15 h at 90° C. under argon and is filtered on silica gel with toluene. The solvent is removed in vacuum and the product is crystallized from diethyl ether. The product has a glass transition point of 158° C.

$^1$H NMR (300 MHz, THF-d$_8$, ppm): δ=8.57 (d, J=9.2 Hz, 1H), 8.50 (d, J=9.1 Hz, 1H), 8.41 (d, J=2.5 Hz, 1H), 8.08 (d, J=8.4 Hz, 1H), 7.73-7.94 (m, 8H), 6.65-7.53 (m, 30H).

Example 2

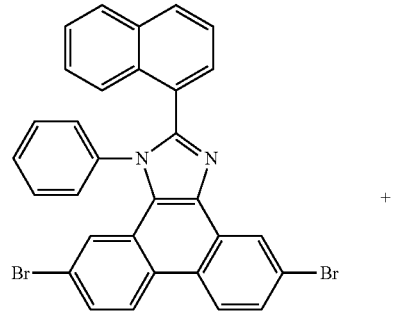

+

Example 3

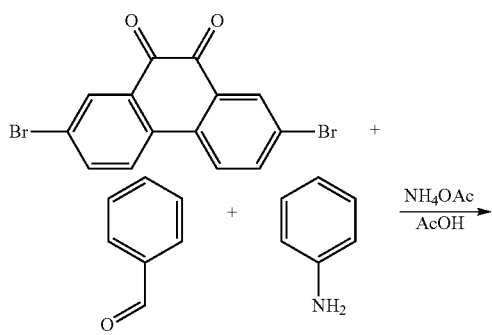

3a) 10.0 g (82.0 mmol) 2,7-dibromo-phenanthrene-9,10-dione, 3.19 g (30.1 mmol) benzaldehyde, 5.09 g (54.6 mmol) aniline and 6.32 g (82.0 mmol) ammonium acetate in 150 ml glacial acetic acid are refluxed for 23 h under nitrogen. The product is filtered off, washed with glacial acetic acid, water, a sodium hydrogen carbonate solution and water, then decocted in isoporpanol and filtered on silica gel with toluene.

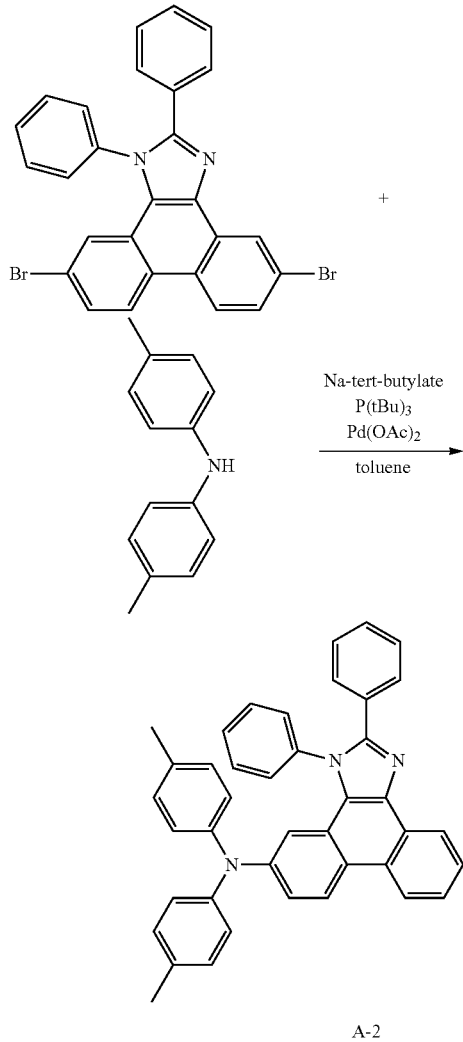

3b) 2.73 g (28.4 mmol) sodium tert-butylate are added to 5.00 g (9.46 mmol) of the product of example 3a in 50 ml toluene. The reaction mixture is degassed with argon. 106 mg (0.47 mmol) palladium(II) acetate are added. The reaction mixture is degassed with argon. 0.95 ml (0.95 mmol) of a 1M solution of tri-tert-butylphosphine in toluene are added. A degassed solution of 5.60 g (28.4 mmol) di-p-tolyl-amine is added. The reaction mixture is stirred for 20 h at 100° C. under argon. The reaction mixture is washed with 60 ml 1% sodium cyanide solution. The organic solvent is removed in vacuum. The product is decocted with ethanol, dissolved in dichloromethane and ethanol is added. The dichloromethane is distilled off. The product is filtered off (melting point: 239° C.).

$^1$H NMR (300 MHz, THF-$d_8$, ppm): δ=8.48 (t, J=9.6 Hz, 2H), 8.42 (d, J=2.4 Hz, 2H), 6.46-7.49 (m, 2H), 7.02-7.33 (m, 22H), 6.81-6.87 (m, 5H), 3.36 (s, 6H), 3.33 (s, 6H).

Device Fabrication and Application Examples

Devices are fabricated by thermal evaporation in high vacuum (<10$^{-6}$ mbar). The anode consists of ca. 1200 Å of indium tin oxide (ITO) previously deposited on a glass substrate. The cathode consists of 1000 Å of Al. All devices are tested immediately after preparation, without encapsulation, in the nitrogen atmosphere of a glove box (<1 ppm of $H_2O$ and $O_2$). All materials used are of sublimed quality.

Application Example 1

The organic stack consists sequentially, from the ITO surface, of 600 Å compound A-11 co-evaporated in a 10:1 evaporation rate ratio with 4F-TCNQ as hole transport layer, followed by 10 Å compound A-11 as the electron blocking layer. The emissive layer consists of 200 Å of compound A-11 as host doped with 10% of red emitter, iridium(III)bis(2-methyldibenzo[th]quinoxaline) (acetylacetonate), followed by 100 Å of BAlq (bis(2-methyl-8-quinolinolato)-4-(phenyl-phenolato)aluminium-(III) as the hole blocking layer and 600 Å of electron transport material composed of BPhen (4,7 diphenyl-1,10-phenantroline) doped with 6% Cs.

Application Example 2

The same as application example 1, except that 4,4'-bis[N-(1-naphtyl)-N-phenylamino]biphenyl (α-NPD) is used as host instead of compound A-11.

Application Example 3

The same as application example 2, except that 4,4'-bis[N-(1-naphtyl)-N-phenylamino]biphenyl (α-NPD) is used as the electron blocking layer instead of compound A-11

Application Example 4

The same as application example 1, except that 4,4'-bis[N-(1-naphtyl)-N-phenylamino]biphenyl (α-NPD) doped with 4F-TCNQ (10:1) is used as hole transport layer instead of compound A-11.

Application Example 5

The same as application example 4, except that 4,4'-bis[N-(1-naphtyl)-N-phenylamino]biphenyl (α-NPD) is used as host instead of compound A-11.

Application Example 6

The same as application example 4, except that 4,4'-bis[N-(1-naphtyl)-N-phenylamino]biphenyl (α-NPD) is used as the electron blocking layer instead of compound A-11.

Comparative Application Example 1

The organic stack consisted sequentially, from the ITO surface, of 600 Å 4,4'-bis[N-(1-naphtyl)-N-phenylamino]biphenyl (α-NPD) co-evaporated in a 10:1 evaporation rate ratio with 4F-TCNQ as hole transport layer, followed by 100 Å α-NPD as the electron blocking layer. The emissive layer consists of 200 Å of α-NPD as host doped with 10% of red emitter, iridium(III)bis(2-methyldibenzo[th]quinoxaline) (acetylacetonate), followed by 100 Å of BAlq (bis(2-methyl-8-quinolinolato)-4-(phenyl-phenolato)aluminium-(III) as the hole blocking layer and 600 Å of electron transport material composed of BPhen (4,7 diphenyl-1,10-phenantroline) doped with 6% Cs.

The luminous efficiency, along with the onset voltage (@1000 cd/m$^2$) and maximum luminance measured for devices prepared as above is reported in the table below:

| | C. Eff@1000 [cd/m²] | V@1000 [cd/m²] | Max Lum/[cd/m²] | T₅₀ (4500 cd/m²)[1] |
|---|---|---|---|---|
| Appl. Ex. 1 | 13 | 2.5 | 18700 | 1000 |
| Appl. Ex. 2 | 16 | 2.8 | 23300 | 3300 |
| Appl. Ex. 3 | 16 | 2.7 | 21700 | 2100 |
| Appl. Ex. 4 | 12 | 2.5 | 19000 | 3300 |
| Appl. Ex. 5 | 14 | 2.8 | 21000 | 5000 |
| Appl. Ex. 6 | 16 | 2.5 | 20000 | 1100 |
| Comp. Appl. Ex. 1 | 16 | 3 | 24500 | 3000 |

[1]Time after which an OLED device with a luminance of 4500 cd/m² achieves 50% of the initial luminance.

Depending on the device architecture the devices of the present invention have a lower onset voltage and can show a superior lifetime in comparison to the device of the Comparative Application Example 1 at comparable luminous efficiency and maximum luminance.

Example 4

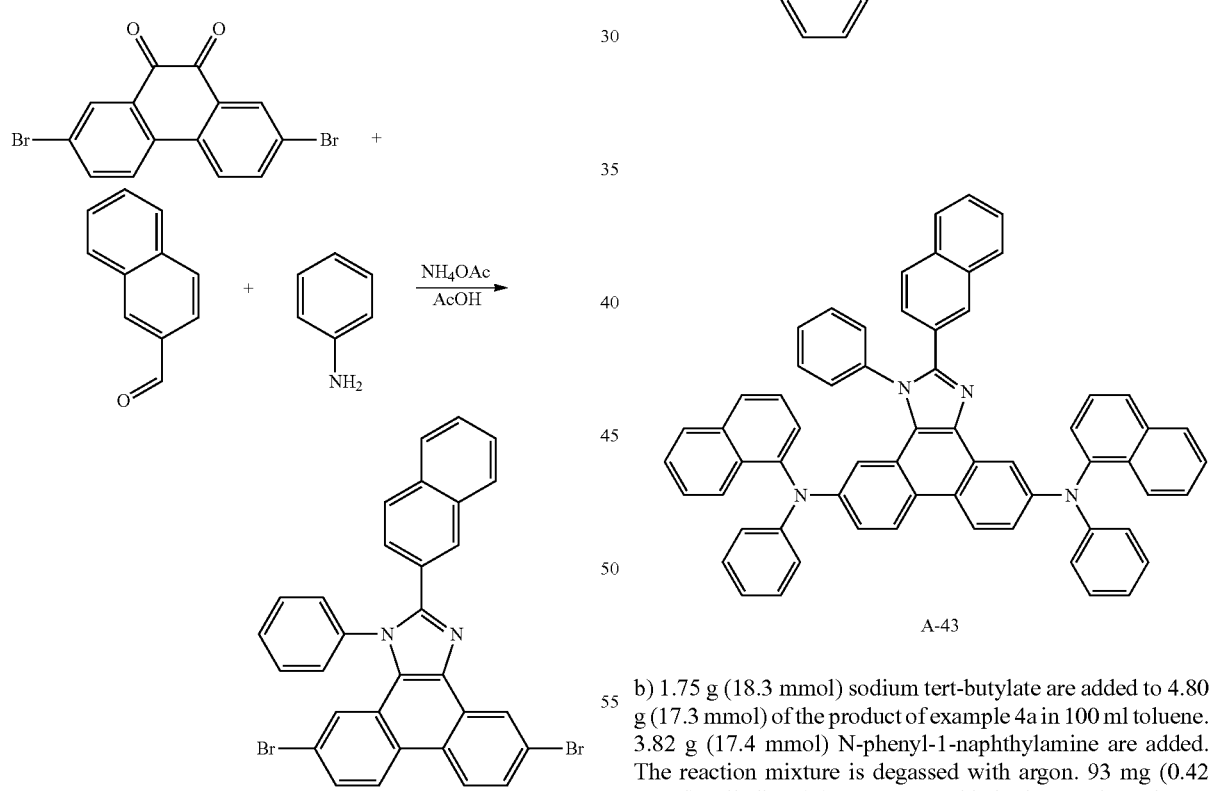

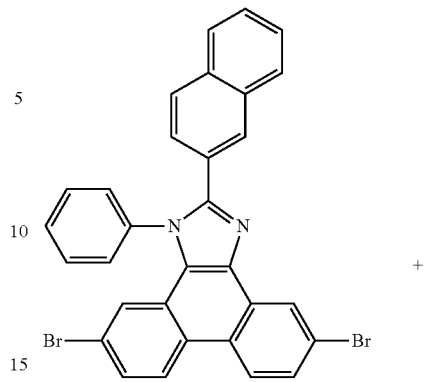

a) 5.0 g (13.6 mmol) 2,7-dibromo-phenanthrene-9,10-dione, 2.35 g (15.0 mmol) 2-naphthalene carboxaldehyde, 2.54 g (27.3 mmol) aniline and 3.16 g (41.0 mmol) ammonium acetate in 80 ml glacial acetic acid are refluxed for 18 h under nitrogen. The product is filtered off, washed with glacial acetic acid, water, a sodium hydrogen carbonate solution and water and then decocted in diethyl-ether.

b) 1.75 g (18.3 mmol) sodium tert-butylate are added to 4.80 g (17.3 mmol) of the product of example 4a in 100 ml toluene. 3.82 g (17.4 mmol) N-phenyl-1-naphthylamine are added. The reaction mixture is degassed with argon. 93 mg (0.42 mmol) palladium(II) acetate are added. The reaction mixture is degassed with argon. 170 mg (83 mmol) tri-tert-butylphosphine are added. The reaction mixture is degassed with argon. The reaction mixture is stirred for 21 h at 90° C. under argon and is filtered on silica gel with toluene. The solvent is removed in vacuum and the product is decocted in diethylether. Column chromatography on silica gel with toluene/cyclohexane 1/1 and than toluene/cyclohexane 7/3 results in the compound A-43 (yield: 51%).

¹H NMR (300 MHz, THF-d₈, ppm): δ=8.52 (d, J=2.4 Hz, 1H), 8.49 (d, J=9.3 Hz, 1H), 8.42 (d, J=9.1 Hz, 1H), 8.42 (d, J=9.1 Hz, 1H), 8.06 (d, J=8.5 Hz, 1H), 6.87-7.95 (m, 36H), 6.74 (d, J=2.3 Hz, 1H).

J=8.5 Hz, 1H), 7.91 (t, J=8.8 Hz, 2H), 7.76-7.81 (m, 2H), 7.70 (d, J=8.5 Hz, 1H), 7.05-7.53 (m, 23H), 6.85-6.94 (m, 7H), 6.68 (d, J=2.4 Hz, 1H).

Example 5

Example 6

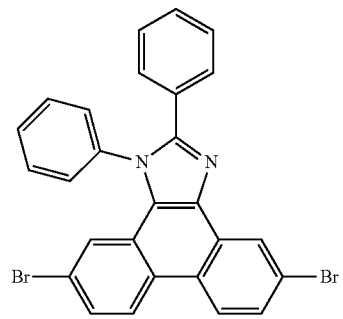

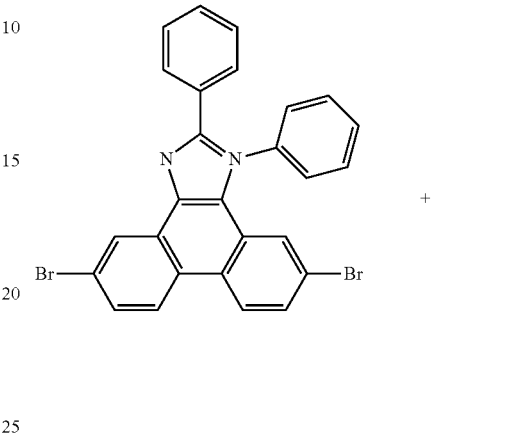

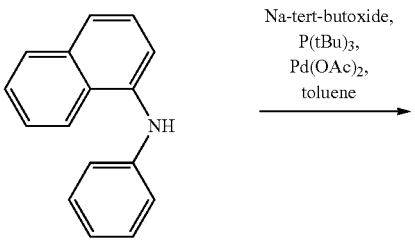

Na-tert-butoxide,
P(tBu)₃,
Pd(OAc)₂,
toluene
⟶

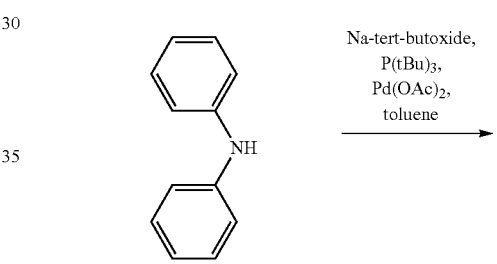

Na-tert-butoxide,
P(tBu)₃,
Pd(OAc)₂,
toluene
⟶

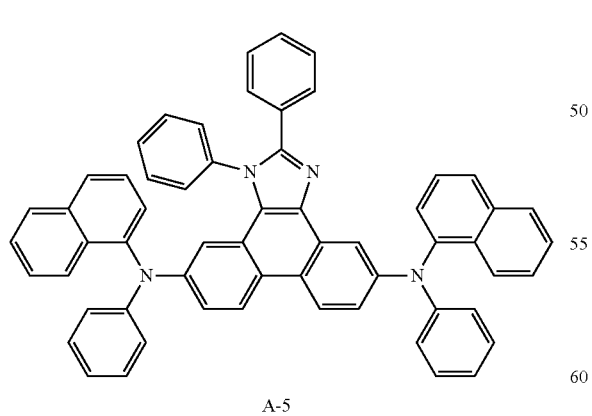

A-5

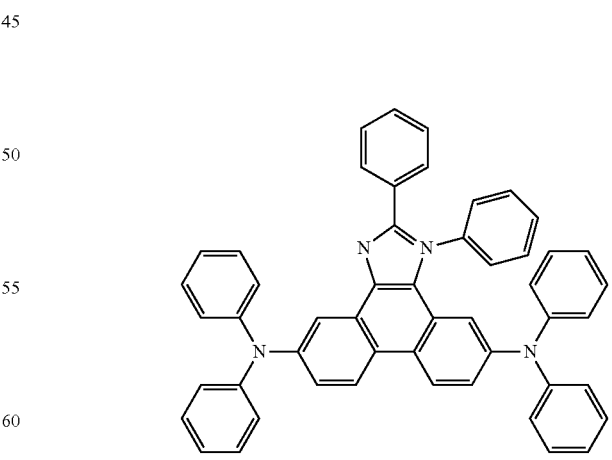

A-1

Cpd. A-5 is prepared in analogy to example 1b starting from the product of example 3a and N-phenyl-1-naphthylamine. Melting point: 290° C. ¹H NMR (300 MHz, THF-d₈, ppm): δ=8.45-8.48 (m, 2H), 8.41 (d, J=9.1 Hz, 1H), 8.05 (d, Cpd. A-1 is prepared in analogy to example 1b starting from the product of example 3a and N,N-diphenylamine. Melting point: 277° C. ¹H NMR (300 MHz, THF-d₈, ppm):

δ=8.57 (t, J=9.7 Hz, 2H), 8.49 (d, J=2.5 Hz, 1H), 7.48-7.52 (m, 2H), 7.15-7.35 (m, 22H), 7.89-7.06 (m, 9H).

Example 6

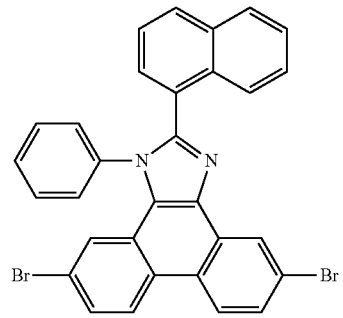

+

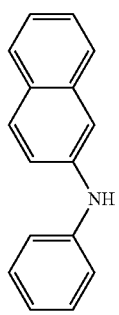

→ Na-tert-butoxide, P(tBu)₃, Pd(OAc)₂, toluene

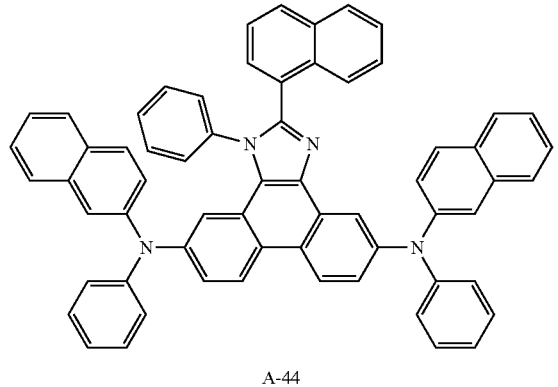

A-44

Cpd. A-44 is prepared in analogy to example 1b starting from the product of example 1a and N-phenyl-2-naphthylamine. Melting point: 268° C. $^1$H NMR (300 MHz, THF-$d_8$, ppm): δ=8.63 (d, J=9.2 Hz, 1H), 8.59 (d, J=9.1 Hz, 1H), 8.45 (d, J=2.5 Hz, 1H), 6.88-7.96 (m, 35H), 6.47-6.56 (m, 4H), 7.77-7.82 (m, 2H), 6.80-7.45 (m, 40H).

Example 7

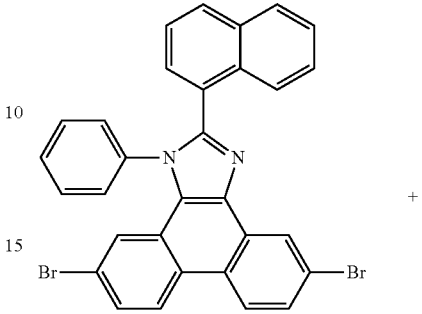

+

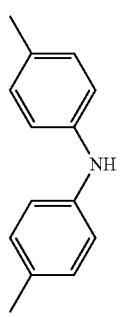

→ Na-tert-butoxide, P(tBu)₃, Pd(OAc)₂, toluene

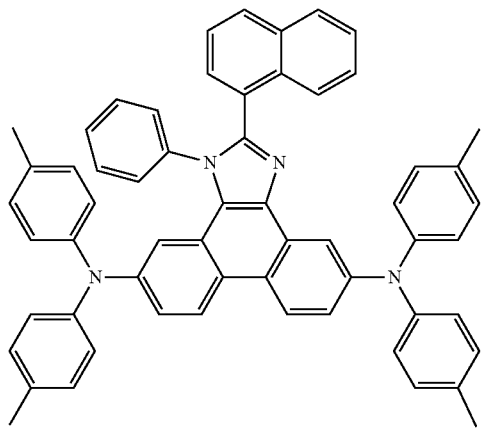

A-8

Cpd. A-8 is prepared in analogy to example 1b starting from the product of example 1a and N,N-bis(4-methylphenyl)amine. Melting point: 286° C. $^1$H NMR (300 MHz, THF-$d_8$, ppm): δ=8.54 (d, J=9.2 Hz, 1H), 8.50 (d, J=9.2 Hz, 1H), 8.36 (d, J=2.5 Hz, 1H), 7.94-7.97 (m, 1H), 7.94-7.97 (m, 2H), 7.77-7.82 (m, 2H), 6.80-7.45 (m, 40H).

Example 8

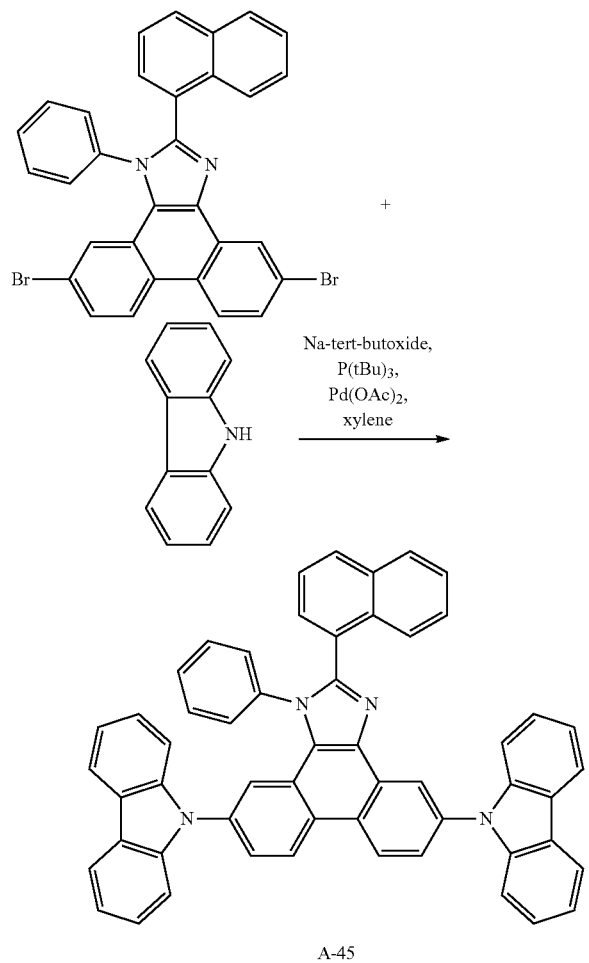

Cpd. A-45 is prepared in analogy to example 1b starting from the product of example 1a and carbazole. Xylene is used as solvent for this reaction. Melting point: 286° C. $^1$H NMR (300 MHz, THF-d$_8$, ppm): δ=9.18 (d, J=2.2 Hz, 1H), 9.09 (d, J=9.1 Hz, 1H), 9.04 (d, J=9.0 Hz, 1H), 8.20 (d, J=7.7 Hz, 2H), 8.14 (d, J=7.07 Hz, 2H), 7.05-8.06 (m, 27H).

Application Example 7

The organic stack consists sequentially, from the ITO surface, of 600 Å compound NPD co-evaporated in a 10:1 evaporation rate ratio with 4F-TCNQ as hole transport layer, followed by 100 Å compound cpd. A-44 as the electron blocking layer. The emissive layer consists of 200 Å of 4,4'-bis[N-(1-naphtyl)-N-phenylamino]biphenyl (α-NPD) as host doped with 10% of red emitter, iridium(III)bis(2-methyldibenzo[th] quinoxaline) (acetylacetonate), followed by 100 Å of BAlq (bis(2-methyl-8-quinolinolato)-4-(phenyl-phenolato)aluminium-(III) as the hole blocking layer and 600 Å of electron transport material composed of BPhen (4,7 diphenyl-1,10-phenantroline) doped with 6% Cs.

Comparative Application Example 2

The organic stack consisted sequentially, from the ITO surface, of 600 Å 4,4'-bis[N-(1-naphtyl)-N-phenylamino]biphenyl (α-NPD) co-evaporated in a 10:1 evaporation rate ratio with 4F-TCNQ as hole transport layer, followed by 100 Å α-NPD as the electron blocking layer. The emissive layer consists of 200 Å of α-NPD as host doped with 10% of red emit-ter, iridium(III)bis(2-methyldibenzo[f,h]quinoxaline) (acetylacetonate), followed by 100 Å of BAlq (bis(2-methyl-8-quinolinolato)-4-(phenyl-phenolato)aluminium-(III) as the hole blocking layer and 600 Å of electron transport material composed of BPhen (4,7 diphenyl-1,10-phenantroline) doped with 6% Cs.

Application Example 8

The same as comparative example 1, except that cpd. A-44 co-evaporated in a 10:1 evaporation rate ratio with 4F-TCNQ is used as the hole transport layer instead of 4,4'-bis[N-(1-naphtyl)-N-phenylamino]biphenyl (α-NPD) co-evaporated in a 10:1 evaporation rate ratio with 4F-TCNQ.

Application Example 9

The organic stack consists sequentially, from the ITO surface, of 600 Å compound NPD co-evaporated in a 10:1 evaporation rate ratio with 4F-TCNQ as hole transport layer, followed by 100 Å compound A-2 as the electron blocking layer. The emissive layer consists of 200 Å of 4,4'-bis[N-(1-naphtyl)-N-phenylamino]biphenyl (α-NPD) as host doped with 10% of red emitter, iridium(III)bis(2-methyldibenzo[th]quinoxaline) (acetylacetonate), followed by 100 Å of BAlq (bis (2-methyl-8-quinolinolato)-4-(phenyl-phenolato)aluminium-(III) as the hole blocking layer and 600 Å of electron transport material composed of BPhen (4,7 diphenyl-1,10-phenantroline) doped with 6% Cs.

The luminous efficiency, along with the onset voltage (@1000 cd/m$^2$) and maximum luminance measured for devices prepared as above is reported in the table below:

|  | C. Eff@1000 [cd/m$^2$] | V@1000 [cd/m$^2$] | Max Lum/[cd/m$^2$] | T$_{50}$ (4500 cd/m$^2$)[1] |
|---|---|---|---|---|
| Appl. Ex. 7 | 15.1 | 3.3 | 20200 | 1800 |
| Appl. Ex. 8 | 15.1 | 2.6 | 21000 | 780 |
| Appl. Ex. 9 | 15.2 | 3.1 | 23600 | 2100 |
| Comp. Appl. Ex. 2 | 15.6 | 2.7 | 21900 | 840 |

[1]Time after which an OLED device with a luminance of 4500 cd/m$^2$ achieves 50% of the initial luminance.

Depending on the device architecture the devices of the present invention have a lower voltage or can show a superior lifetime in comparison to the device of the Comparative Application Example 2 at comparable luminous efficiency and maximum luminance.

The invention claimed is:
1. An electroluminescent (EL) device, comprising
(a) an anode,
(b) a hole transporting/injecting layer,
(c) optionally an electron blocking layer,
(d) a light-emitting layer,
(e) optionally a hole- or exciton-blocking layer,
(f) an electron-transporting layer, and
(g) a cathode, wherein:

the hole transporting/injecting layer, (b) the electron blocking layer (c), or both layers of (b) and (c), comprises a compound of the formula (I)

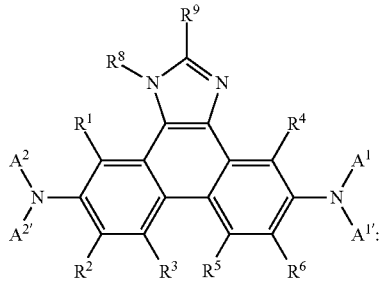

$R^1$ and $R^4$ are independently of each other hydrogen, $C_1$-$C_{18}$alkyl, $C_1$-$C_{18}$alkyl which is substituted by E, interrupted by D, or both, $C_1$-$C_{18}$perfluoroalkyl, $C_2$-$C_{18}$alkenyl, $C_2$-$C_{18}$alkynyl, $C_1$-$C_{18}$alkoxy, $C_1$-$C_{18}$alkoxy which is substituted by E, interrupted by D, or both, CN, or —CO—$R^{28}$;

$R^2$, $R^3$, $R^5$ and $R^6$ are independently of each other H, $C_1$-$C_{18}$alkyl, $C_1$-$C_{18}$alkyl which is substituted by E, interrupted by D, or both, $C_1$-$C_{18}$perfluoroalkyl, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E, interrupted by D, or both, $C_7$-$C_{25}$aralkyl, CN, or —CO—$R^{28}$, wherein, optionally, at least one combination of i) $R^2$ and $R^3$ and ii) $R^5$ and $R^6$ form a group:

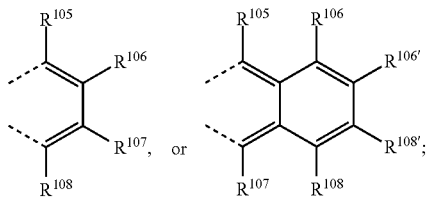

$R^8$ is $C_1$-$C_{18}$alkyl, $C_1$-$C_{18}$alkyl which is substituted by E, interrupted by D, or both, $C_1$-$C_{18}$perfluoroalkyl, $C_6$-$C_{24}$aryl, $C_6$-$C_{24}$aryl which is substituted by G, $C_2$-$C_{20}$heteroaryl, or $C_2$-$C_{20}$heteroaryl which is substituted by G, $R^9$ is H, $C_1$-$C_{18}$alkyl, $C_1$-$C_{18}$alkyl which is substituted by E, interrupted by D, or both, $C_1$-$C_{18}$perfluoroalkyl, $C_6$-$C_{24}$aryl, $C_6$-$C_{24}$aryl which is substituted by G, $C_2$-$C_{20}$heteroaryl, or $C_2$-$C_{20}$heteroaryl which is substituted by G, $R^{105}$, $R^{106}$, $R^{107}$, $R^{108}$, $R^{106'}$ and $R^{108'}$ are independently of each other H, $C_1$-$C_{18}$alkyl, $C_1$-$C_{18}$alkyl which is substituted by E, interrupted by D, or both, $C_1$-$C_{18}$alkoxy, or $C_1$-$C_{18}$alkoxy which is substituted by E, interrupted by D, or both;

$A^1$, $A^2$, $A^{1'}$ and $A^{2'}$ are independently of each other a group of formula

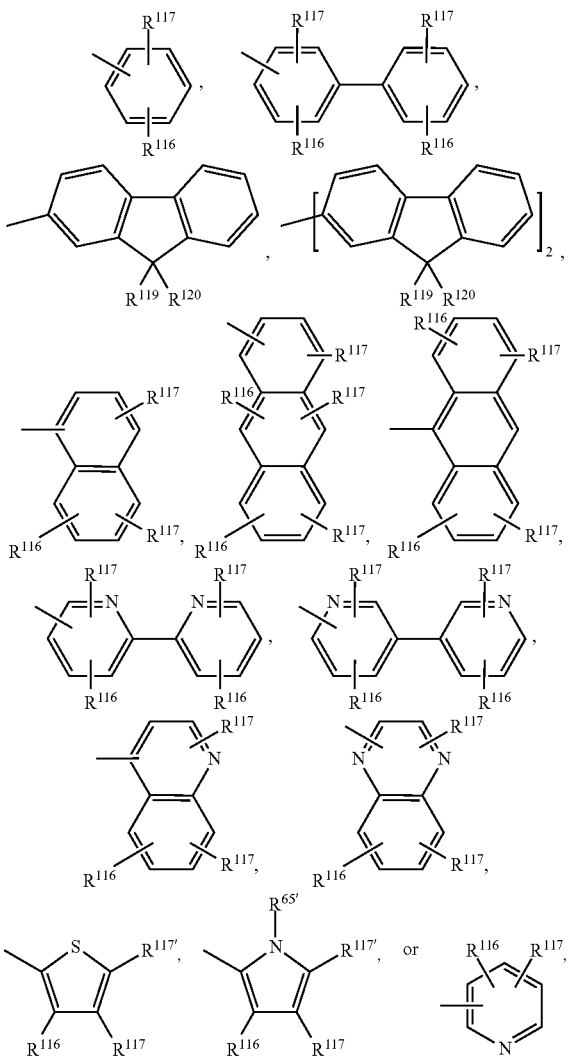

or $A^1$ and $A^{1'}$, $A^2$ and $A^{2'}$, or both $A^1$ and $A^{1'}$ and $A^2$ and $A^{2'}$, together with the nitrogen atom to which they are bonded form a heteroaromatic ring, or ring system;

$R^{41}$ can be the same or different at each occurrence and is Cl, F, CN, N($R^{45}$)$_2$, a $C_1$-$C_{25}$alkyl group, a $C_4$-$C_{18}$cycloalkyl group, a $C_1$-$C_{25}$alkoxy group, in which one or more carbon atoms which are not adjacent to each other are optionally replaced by —N$R^{45}$—, —O—, —S—, or —C(=O)—O—, and/or wherein one or more hydrogen atoms are optionally replaced by F, a $C_6$-$C_{24}$aryl group, or a $C_6$-$C_{24}$aryloxy group, wherein one or more carbon atoms are optionally replaced by O, S, or N, and/or which are optionally substituted by one or more non-aromatic groups $R^{41}$, or two or more groups $R^{41}$ form a ring system;

$R^{45}$ is H, a $C_1$-$C_{25}$alkyl group, a $C_4$-$C_{18}$cycloalkyl group, in which one or more carbon atoms which are not adjacent to each other are optionally replaced by —N$R^{45''}$—, —O—, —S—, —C(=O)—O—, or, —O—C(=O)—O—, and/or wherein one or more hydrogen atoms are optionally replaced by F, a $C_6$-$C_{24}$aryl group, or a $C_6$-$C_{24}$aryloxy group, wherein one or more carbon atoms are optionally replaced by O, S, or N, and/or which are optionally substituted by one or more non-aromatic groups $R^{41}$;

R⁴⁵" is H, a $C_1$-$C_{25}$alkyl group, or a $C_4$-$C_{18}$cycloalkyl group;

R⁶⁵' is H, a $C_1$-$C_{25}$alkyl group, a $C_4$-$C_{18}$cycloalkyl group, in which one or more carbon atoms which are not adjacent to each other are optionally replaced by —O—, or —S—, and/or wherein one or more hydrogen atoms are optionally replaced by F, a $C_6$-$C_{24}$aryl group, or a $C_6$-$C_{24}$aryloxy group, wherein one or more carbon atoms are optionally replaced by O, S, or N, and/or which are optionally substituted by G;

R¹¹⁶, R¹¹⁷ and R¹¹⁷' are independently of each other H, halogen, —CN, $C_1$-$C_{18}$alkyl, $C_1$-$C_{18}$alkyl which is substituted by E, interrupted by D, or both, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E, interrupted by D, or both, $C_7$-$C_{25}$aralkyl, —C(=O)—R¹²⁷', —C(=O)OR¹²⁷', or —C(=O)NR¹²⁷R¹²⁶, or substituents R¹¹⁶, R¹¹⁷ and R¹¹⁷', which are adjacent to each other, can form a ring;

R¹¹⁹ and R¹²⁰ are independently of each other $C_1$-$C_{18}$alkyl, $C_1$-$C_{18}$alkyl which is substituted by E, interrupted by D, or both, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E, interrupted by D, or both, or $C_7$-$C_{25}$aralkyl, or R¹¹⁹ and R¹²⁰ together form a group of formula =CR¹²¹R¹²², wherein R¹²¹ and R¹²² are independently of each other H, $C_1$-$C_{18}$alkyl, $C_1$-$C_{18}$alkyl which is substituted by E, interrupted by D, or both, $C_6$-$C_{24}$aryl, $C_6$-$C_{24}$aryl which is substituted by G, $C_2$-$C_{20}$heteroaryl, or $C_2$-$C_{20}$heteroaryl which is substituted by G, or R¹¹⁹ and R¹²⁰ together form a five or six membered ring, optionally substituted by $C_1$-$C_{18}$alkyl, $C_1$-$C_{18}$alkyl which is substituted by E, interrupted by D, or both, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E, interrupted by D, or both, $C_7$-$C_{25}$aralkyl, or —C(=O)—R¹²⁷'; and R¹²⁶, R¹²⁷ and R¹²⁷' are independently of each other $C_6$-$C_{18}$aryl, $C_6$-$C_{18}$aryl which is substituted by $C_1$-$C_{18}$alkyl, or $C_1$-$C_{18}$alkoxy, $C_1$-$C_{18}$alkyl, or $C_1$-$C_{18}$alkyl which is interrupted by —O—;

D is —CO—, —COO—, —S—, —SO—, —SO₂—, —O—, —NR²⁵—, —SiR³⁰R³¹—, —POR³²—, —CR²³=CR²⁴—, or —C≡C—;

E is —OR²⁹, —SR²⁹, —NR²⁵R²⁶, —COR²⁸, —COOR²⁷, —CONR²⁵R²⁶, —CN, or halogen;

G is E, $C_1$-$C_{18}$alkyl, $C_1$-$C_{18}$alkyl which is interrupted by D, $C_1$-$C_{18}$perfluoroalkyl, $C_1$-$C_{18}$alkoxy, or $C_1$-$C_{18}$alkoxy which is substituted by E, interrupted by D, or both;

R²³ and R²⁴ are independently of each other $C_6$-$C_{18}$aryl, $C_6$-$C_{18}$aryl which is substituted by $C_1$-$C_8$alkyl or $C_1$-$C_8$alkoxy, $C_1$-$C_8$alkyl, or $C_1$-$C_8$alkyl which is interrupted by —O—;

R²⁵ and R²⁶ are independently of each other $C_6$-$C_{18}$aryl, $C_6$-$C_{18}$aryl which is substituted by $C_1$-$C_{18}$alkyl or $C_1$-$C_{18}$alkoxy, $C_1$-$C_{18}$alkyl, or $C_1$-$C_{18}$alkyl which is interrupted by —O—, or R²⁵ and R²⁶ together form a five or six membered ring;

R²⁷ and R²⁸ are independently of each other $C_6$-$C_{18}$aryl, $C_6$-$C_{18}$aryl which is substituted by $C_1$-$C_{18}$alkyl or $C_1$-$C_{18}$alkoxy, $C_1$-$C_{18}$alkyl, or $C_1$-$C_{18}$alkyl which is interrupted by —O—;

R²⁹ is $C_6$-$C_{18}$aryl, $C_6$-$C_{18}$aryl which is substituted by $C_1$-$C_{18}$alkyl or $C_1$-$C_{18}$alkoxy, $C_1$-$C_{18}$alkyl, or $C_1$-$C_{18}$alkyl which is interrupted by —O—;

R³⁰ and R³¹ are independently of each other $C_1$-$C_{18}$alkyl, $C_6$-$C_{18}$aryl, or $C_6$-$C_{18}$aryl which is substituted by $C_1$-$C_{18}$alkyl; and R³² is $C_1$-$C_{18}$alkyl, $C_6$-$C_{18}$aryl, or $C_6$-$C_{18}$aryl which is substituted by $C_1$-$C_{18}$alkyl.

2. The device of claim 1, wherein R¹, R², R³, R⁴, R⁵ and R⁶ are hydrogen.

3. The device of claim 1, wherein:

A¹, A¹', A² and A²' are independently of each other a group of formula

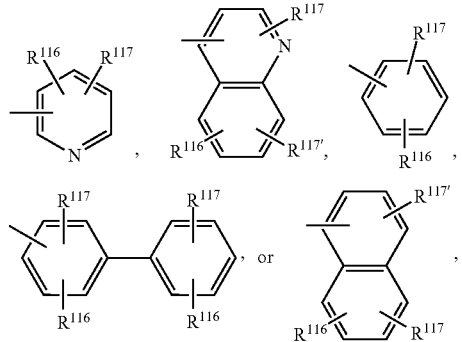

or A¹ and A¹' together with the nitrogen atom to which they are bonded form a group of formula

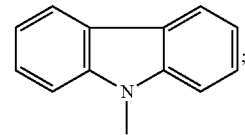

R¹¹⁶, R¹¹⁷ and R¹¹⁷' are independently of each other H, or $C_1$-$C_{18}$alkyl.

4. The device of claim 1, wherein:

R⁸ is $C_1$-$C_{18}$alkyl, $C_1$-$C_{18}$alkyl which is interrupted by D, $C_1$-$C_{18}$perfluoroalkyl, $C_6$-$C_{18}$aryl which may optionally be substituted by $C_1$-$C_{18}$alkyl, $C_1$-$C_{18}$perfluoroalkyl, $C_1$-$C_{18}$alkoxy, or $C_1$-$C_{18}$alkoxy which is interrupted by D;

R⁹ is H, $C_1$-$C_{18}$alkyl, $C_1$-$C_{18}$alkyl, which is interrupted by D, $C_1$-$C_{18}$perfluoroalkyl, $C_6$-$C_{18}$aryl which may optionally be substituted by $C_1$-$C_{18}$alkyl, $C_1$-$C_{18}$perfluoroalkyl, $C_1$-$C_{18}$alkoxy, or $C_1$-$C_{18}$alkoxy which is interrupted by D;

D is —O—, —S—, or —NR²⁵—; and

R²⁵ is $C_6$-$C_{18}$aryl, $C_6$-$C_{18}$aryl which is substituted by $C_1$-$C_{18}$alkyl or $C_1$-$C_{18}$alkoxy, $C_1$-$C_{18}$alkyl, or $C_1$-$C_{18}$alkyl which is interrupted by —O.

5. The device of claim 1, wherein:
the compound of formula (I) is a compound of formula (Ia)

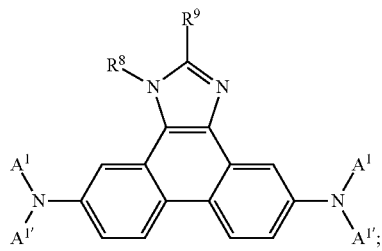
(Ia)

$A^1$ and $A^{1'}$ are independently of each other a group of formula

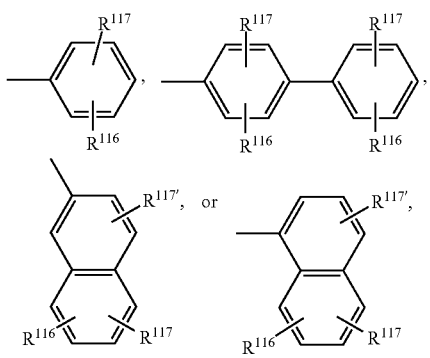

$R^{116}$, $R^{117}$ and $R^{117'}$ are independently of each other H, or $C_1$-$C_{18}$alkyl, or
$A^1$ and $A^{1'}$ together with the nitrogen atom to which they are bonded form a group of formula

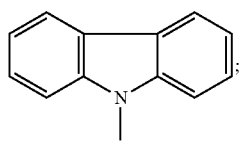

$R^8$ is a group of formula

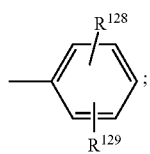

$R^9$ is a group of formula

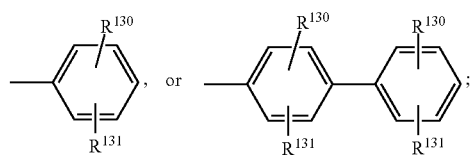

and
$R^{128}$, $R^{129}$, $R^{130}$ and $R^{131}$ are independently of each other H, $C_1$-$C_{18}$alkyl, $C_1$-$C_{18}$alkoxy, or $C_1$-$C_{18}$perfluoroalkyl.

6. The device of claim 1, wherein:
the compound of formula (I) is a compound of formula (Ia):

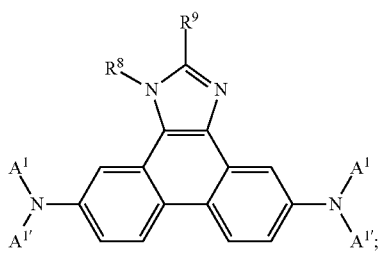
(Ia)

$A^1$ and $A^{1'}$ are independently of each other a group of formula

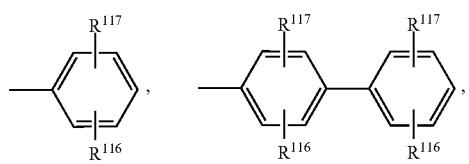

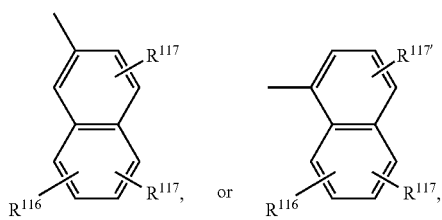

or $A^1$ and $A^{1'}$ together with the nitrogen atom to which they are bonded form a group of formula

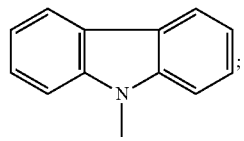

$R^{116}$, $R^{117}$ and $R^{117'}$ are independently of each other H, or $C_1$-$C_{18}$alkyl;
$R^8$ is a group of formula

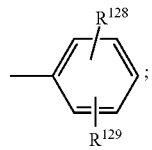

R⁹ is a group of formula

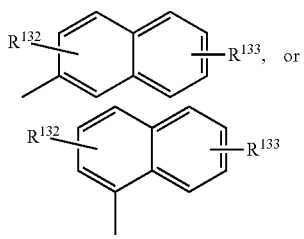

and

R¹²⁸, R¹²⁹, R¹³² and R¹³³ are independently of each other H, $C_1$-$C_{18}$alkyl, $C_1$-$C_{18}$alkoxy, or $C_1$-$C_{18}$perfluoroalkyl.

7. The device of claim 1, wherein the compound of formula (I) is a compound of formula

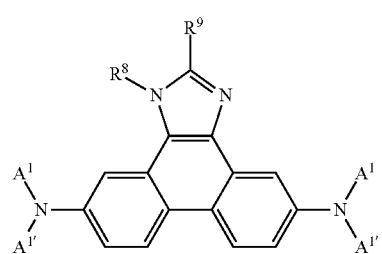

selected from the group consisting of:

| Cpd. | A¹ | A¹' | R⁸ | R⁹ |
|---|---|---|---|---|
| A-1 | phenyl | phenyl | phenyl | phenyl |
| A-2 | 4-methylphenyl | 4-methylphenyl | phenyl | phenyl |
| A-3 | 3-methylphenyl | 3-methylphenyl | phenyl | phenyl |
| A-4 | 2-methylphenyl | 2-methylphenyl | phenyl | phenyl |
| A-5 | phenyl | naphthyl | phenyl | phenyl |
| A-6 | biphenyl | biphenyl | phenyl | phenyl |
| A-7 | phenyl | phenyl | phenyl | naphthyl |
| A-8 | 4-methylphenyl | 4-methylphenyl | phenyl | naphthyl |

-continued

| Cpd. | A¹ | A¹' | R⁸ | R⁹ |
|---|---|---|---|---|
| A-9 | 3-methylphenyl | 3-methylphenyl | phenyl | 1-naphthyl |
| A-10 | 2-methylphenyl | 2-methylphenyl | phenyl | 1-naphthyl |
| A-11 | phenyl | 1-naphthyl | phenyl | 1-naphthyl |
| A-12 | 4-biphenyl | 4-biphenyl | phenyl | 1-naphthyl |
| A-13 | phenyl | phenyl | phenyl | 4-methylphenyl |
| A-14 | 4-methylphenyl | 4-methylphenyl | phenyl | 4-methylphenyl |
| A-15 | 3-methylphenyl | 3-methylphenyl | phenyl | 4-methylphenyl |
| A-16 | 2-methylphenyl | 2-methylphenyl | phenyl | 4-methylphenyl |
| A-17 | phenyl | 1-naphthyl | phenyl | 4-methylphenyl |
| A-18 | 4-biphenyl | 4-biphenyl | phenyl | 4-methylphenyl |
| A-19 | phenyl | phenyl | phenyl | 4-(trifluoromethyl)phenyl |

-continued

| Cpd. | A¹ | A¹' | R⁸ | R⁹ |
| --- | --- | --- | --- | --- |
| A-20 | 4-methylphenyl | 4-methylphenyl | phenyl | 4-(trifluoromethyl)phenyl |
| A-21 | 3-methylphenyl | 3-methylphenyl | phenyl | 4-(trifluoromethyl)phenyl |
| A-22 | 2-methylphenyl | 2-methylphenyl | phenyl | 4-(trifluoromethyl)phenyl |
| A-23 | phenyl | naphthalen-1-yl | phenyl | 4-(trifluoromethyl)phenyl |
| A-24 | biphenyl-4-yl | biphenyl-4-yl | phenyl | 4-(trifluoromethyl)phenyl |
| A-25 | phenyl | phenyl | phenyl | 4-tert-butylphenyl |
| A-26 | 4-methylphenyl | 4-methylphenyl | phenyl | 4-tert-butylphenyl |
| A-27 | 3-methylphenyl | 3-methylphenyl | phenyl | 4-tert-butylphenyl |
| A-28 | 2-methylphenyl | 2-methylphenyl | phenyl | 4-tert-butylphenyl |
| A-29 | phenyl | naphthalen-1-yl | phenyl | 4-tert-butylphenyl |

-continued

| Cpd. | A¹ | A¹' | R⁸ | R⁹ |
|---|---|---|---|---|
| A-30 | 4-biphenyl | 4-biphenyl | phenyl | 4-tert-butylphenyl |
| A-31 | phenyl | phenyl | phenyl | 4-biphenyl |
| A-32 | 4-methylphenyl | 4-methylphenyl | phenyl | 4-biphenyl |
| A-33 | 3-methylphenyl | 3-methylphenyl | phenyl | 4-biphenyl |
| A-34 | 2-methylphenyl | 2-methylphenyl | phenyl | 4-biphenyl |
| A-35 | phenyl | 1-naphthyl | phenyl | 4-biphenyl |
| A-36 | 4-biphenyl | 4-biphenyl | phenyl | 4-biphenyl |
| A-37 | phenyl | phenyl | 3-(trifluoromethyl)phenyl | phenyl |
| A-38 | 4-methylphenyl | 4-methylphenyl | 3-(trifluoromethyl)phenyl | phenyl |
| A-39 | 3-methylphenyl | 3-methylphenyl | 3-(trifluoromethyl)phenyl | phenyl |

-continued

| Cpd. | A¹ | A¹' | R⁸ | R⁹ |
|---|---|---|---|---|
| A-40 | 2-methylphenyl | 2-methylphenyl | 3-(trifluoromethyl)phenyl | phenyl |
| A-41 | phenyl | naphthyl | 3-(trifluoromethyl)phenyl | phenyl |
| A-42 | biphenyl | biphenyl | 3-(trifluoromethyl)phenyl | phenyl |
| A-43 | phenyl | naphthyl | phenyl | naphthyl |
| A-44 | phenyl | naphthyl | phenyl | naphthyl |
| A-45 | 1) | 1) | 3-(trifluoromethyl)phenyl | naphthyl | wherein

1) -NA¹A¹' is 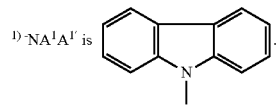

8. The device of claim 1, wherein the hole transporting/injecting layer (b) comprises the compound of formula (I) and a dopant, and
the dopant is at least one selected from the group consisting of titanium oxide ($TiO_x$), vanadium oxide ($VO_x$), molybdenium oxide ($MoO_3$), especially $MO_3$, tungsten oxide ($WO_x$), ruthenium oxide ($RuO_x$), chromium oxide ($CrO_x$), zirconium oxide ($ZrO_x$), hafnium oxide ($HfO_x$) tantalum oxide ($TaO_x$), silver oxide ($AgO_x$), manganese oxide ($MnO_x$), iron trichloride ($FeCl_3$), antimony pentachloride ($SbCl_5$), a metal phthalocyanine compound, dicyano(phthalocyanato(−1)cobalt(III), a oxocarbon-, pseudooxocarbon- or radialene compound, a dicyano (phthalocyanato(−1)ruthenium(III) compound, 2-(6-di-cyanomethylene-1,3,4,5,7,8-hexafluoro-6H-naphthalen-2-ylidene)-malononitrile,

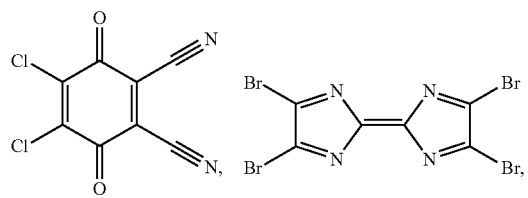

2,3,5,6-tetrafluoro-7,7,8,8-tetracyanoquinodimethane (F$_4$-TCNQ),

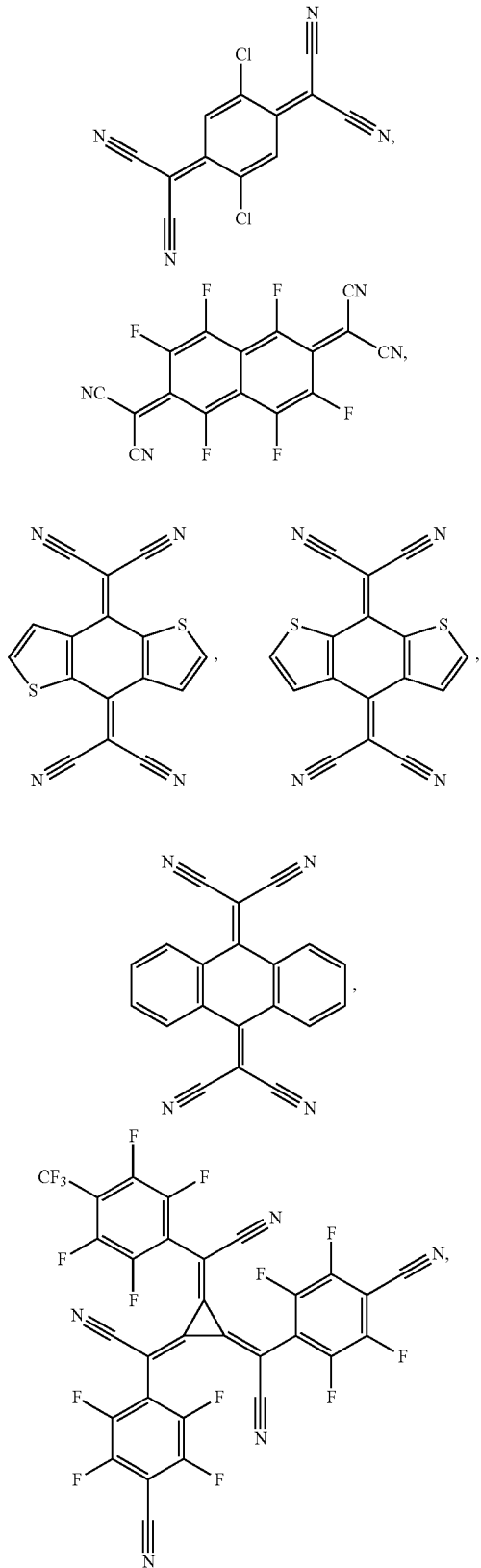

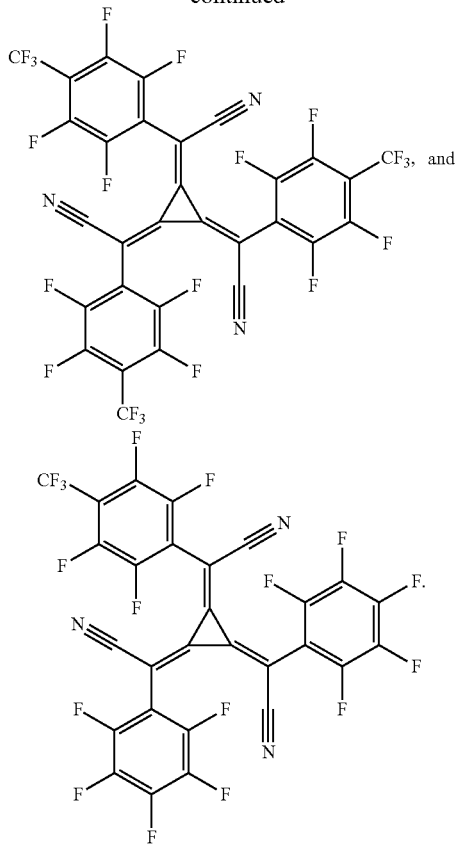

-continued

9. The device of claim 1, wherein the electron blocking layer (c) comprises the compound of formula (I).

10. The device of claim 1, wherein:
A$^1$ and A$^{1'}$, A$^2$ and A$^{2'}$, or A$^1$ and A$^{1'}$ and A$^2$ and A$^{2'}$, together with the nitrogen atom to which they are bonded form a heteroaromatic ring system:

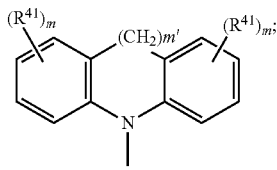

m' is 0, 1, or 2;
m can be the same or different at each occurrence and is 0, 1, 2, or 3;
R$^{41}$ can be the same or different at each occurrence and is Cl, F, CN, N(R$^{45}$)$_2$, a C$_1$-C$_{25}$alkyl group, a C$_4$-C$_{18}$cycloalkyl group, a C$_1$-C$_{25}$alkoxy group, in which one or more carbon atoms which are not adjacent to each other are optionally replaced by —NR$^{45}$—, —O—, —S—, or —C(=O)—O—, and/or wherein one or more hydrogen atoms can be replaced by F, a C$_6$-C$_{24}$aryl group, or a C$_6$-C$_{24}$aryloxy group, wherein one or more carbon atoms can be replaced by O, S, or N, and/or which can be substituted by one or more non-aromatic groups R$^{41}$, or
two or more groups R$^{41}$ form a ring system;
R$^{45}$ is H, a C$_1$-C$_{25}$alkyl group, a C$_4$-C$_{18}$cycloalkyl group, in which one or more carbon atoms which are not adjacent to each other could be replaced by —NR⁴⁵"—, —O—, —S—, —C(=O)—O—, or, —O—C(=O)—O—, and/or wherein one or more hydrogen atoms can be replaced by F, a $C_6$-$C_{24}$aryl group, or a $C_6$-$C_{24}$aryloxy group, wherein one or more carbon atoms can be replaced by O, S, or N, and/or which can be substituted by one or more non-aromatic groups $R^{41}$; and $R^{45"}$ is H, a $C_1$-$C_{25}$alkyl group, or a $C_4$-$C_{18}$cycloalkyl group.

11. The device of claim 10, wherein m is 0, 1 or 2.

12. The device of claim 2, wherein:

$A^1$, $A^{1'}$, $A^2$ and $A^{2'}$ are independently of each other a group of formula

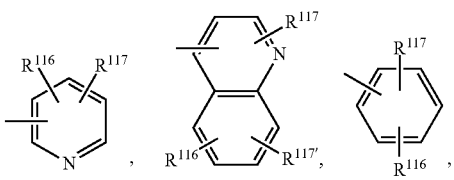

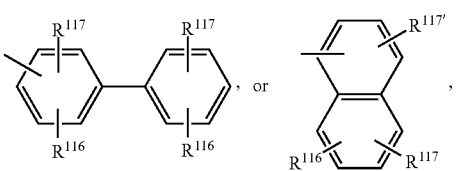

or $A^1$ and $A^{1'}$ together with the nitrogen atom to which they are bonded form a group of formula

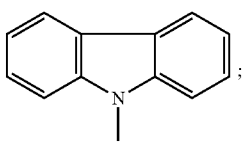

$R^{116}$, $R^{117}$ and $R^{117'}$ are independently of each other H, or $C_1$-$C_{18}$alkyl.

13. The device of claim 2, wherein:

$R^8$ is $C_1$-$C_{18}$alkyl, $C_1$-$C_{18}$alkyl which is interrupted by D, $C_1$-$C_{18}$perfluoroalkyl, $C_1$-$C_{18}$aryl which may optionally be substituted by $C_1$-$C_{18}$alkyl, $C_1$-$C_{18}$perfluoroalkyl, $C_1$-$C_{18}$alkoxy, or $C_1$-$C_{18}$alkoxy which is interrupted by D;

$R^9$ is H, $C_1$-$C_{18}$alkyl, $C_1$-$C_{18}$alkyl, which is interrupted by D, $C_1$-$C_{18}$perfluoroalkyl, $C_6$-$C_{18}$aryl which may optionally be substituted by $C_1$-$C_{18}$alkyl, $C_1$-$C_{18}$perfluoroalkyl, $C_1$-$C_{18}$alkoxy, or $C_1$-$C_{18}$alkoxy which is interrupted by D;

D is —O—, —S—, or —NR²⁵—; and $R^{25}$ is $C_6$-$C_{18}$aryl, $C_6$-$C_{18}$aryl which is substituted by $C_1$-$C_{18}$alkyl or $C_1$-$C_{18}$alkoxy, $C_1$-$C_{18}$alkyl, or $C_1$-$C_{18}$alkyl which is interrupted by —O.

14. The device of claim 2, wherein:
the compound of formula (I) is a compound of formula (Ia)

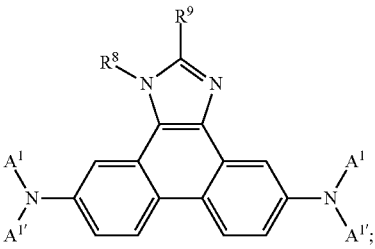

$A^1$ and $A^{1'}$ are independently of each other a group of formula

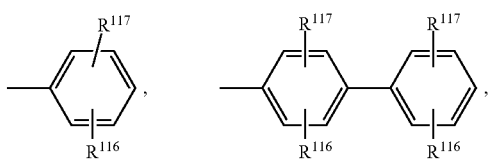

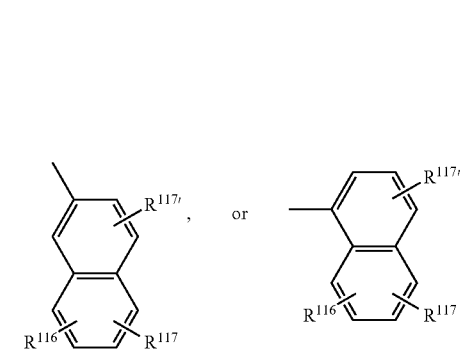

$R^{116}$, $R^{117}$ and $R^{117'}$ are independently of each other H, or $C_1$-$C_{18}$alkyl, or $A^1$ and $A^{1'}$ together with the nitrogen atom to which they are bonded form a group of formula

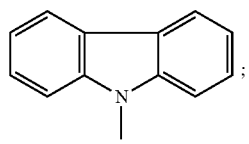

$R^8$ is a group of formula

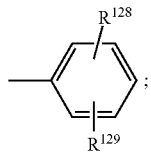

$R^9$ is a group of formula

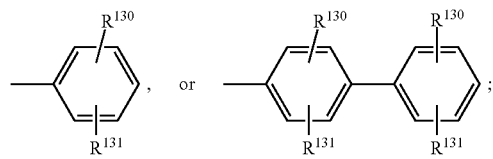

and $R^{128}$, $R^{129}$, $R^{130}$ and $R^{131}$ are independently of each other H, $C_1$-$C_{18}$alkyl, $C_1$-$C_{18}$alkoxy, or $C_1$-$C_{18}$perfluoroalkyl.

15. The device of claim 2, wherein:
the compound of formula (I) is a compound of formula (Ia);

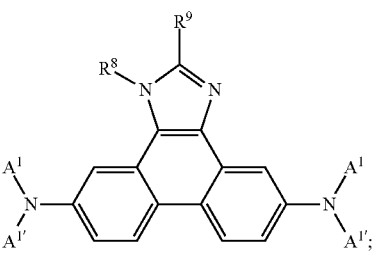

(Ia)

$A^1$ and $A^{1'}$ are independently of each other a group of formula

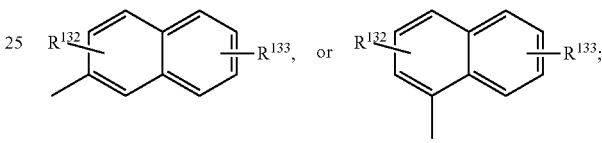

or $A^1$ and $A^{1'}$ together with the nitrogen atom to which they are bonded form a group of formula

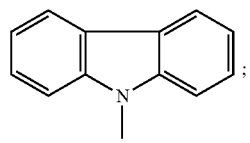

$R^{116}$, $R^{117}$ and $R^{117'}$ are independently of each other H, or $C_1$-$C_{18}$alkyl;

$R^8$ is a group of formula

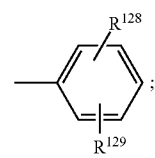

$R^9$ is a group of formula

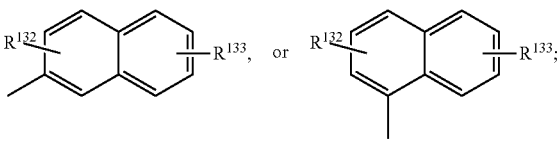

and $R^{128}$, $R^{129}$, $R^{132}$ and $R^{133}$ are independently of each other H, $C_1$-$C_{18}$alkyl, $C_1$-$C_{18}$alkoxy, or $C_1$-$C_{18}$perfluoroalkyl.

16. The device of claim 2, wherein the compound of formula (I) is a compound of formula

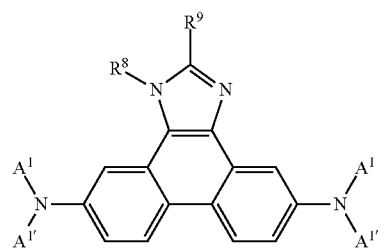

selected from the group consisting of:

| Cpd. | $A^1$ | $A^{1'}$ | $R^8$ | $R^9$ |
|------|-------|----------|-------|-------|
| A-1 | ----⟨phenyl⟩ | ----⟨phenyl⟩ | ----⟨phenyl⟩ | ----⟨phenyl⟩ |
| A-2 | ----⟨phenyl⟩-CH₃ | ----⟨phenyl⟩-CH₃ | ----⟨phenyl⟩ | ----⟨phenyl⟩ |
| A-3 | ----⟨phenyl-CH₃⟩ | ----⟨phenyl-CH₃⟩ | ----⟨phenyl⟩ | ----⟨phenyl⟩ |

-continued

| Cpd. | A¹ | A¹' | R⁸ | R⁹ |
|---|---|---|---|---|
| A-4 | 2-methylphenyl | 2-methylphenyl | phenyl | phenyl |
| A-5 | phenyl | 1-naphthyl | phenyl | phenyl |
| A-6 | 4-biphenyl | 4-biphenyl | phenyl | phenyl |
| A-7 | phenyl | phenyl | phenyl | 1-naphthyl |
| A-8 | 4-methylphenyl | 4-methylphenyl | phenyl | 1-naphthyl |
| A-9 | 3-methylphenyl | 3-methylphenyl | phenyl | 1-naphthyl |
| A-10 | 2-methylphenyl | 2-methylphenyl | phenyl | 1-naphthyl |
| A-11 | phenyl | 1-naphthyl | phenyl | 1-naphthyl |
| A-12 | 4-biphenyl | 4-biphenyl | phenyl | 1-naphthyl |
| A-13 | phenyl | phenyl | phenyl | 4-methylphenyl |

-continued

| Cpd. | A¹ | A¹' | R⁸ | R⁹ |
|---|---|---|---|---|
| A-14 | 4-methylphenyl | 4-methylphenyl | phenyl | 4-methylphenyl |
| A-15 | 3-methylphenyl | 3-methylphenyl | phenyl | 4-methylphenyl |
| A-16 | 2-methylphenyl | 2-methylphenyl | phenyl | 4-methylphenyl |
| A-17 | phenyl | 1-naphthyl | phenyl | 4-methylphenyl |
| A-18 | 4-biphenyl | 4-biphenyl | phenyl | 4-methylphenyl |
| A-19 | phenyl | phenyl | phenyl | 4-(trifluoromethyl)phenyl |
| A-20 | 4-methylphenyl | 4-methylphenyl | phenyl | 4-(trifluoromethyl)phenyl |
| A-21 | 3-methylphenyl | 3-methylphenyl | phenyl | 4-(trifluoromethyl)phenyl |
| A-22 | 2-methylphenyl | 2-methylphenyl | phenyl | 4-(trifluoromethyl)phenyl |
| A-23 | phenyl | 1-naphthyl | phenyl | 4-(trifluoromethyl)phenyl |
| A-24 | 4-biphenyl | 4-biphenyl | phenyl | 4-(trifluoromethyl)phenyl |

-continued

| Cpd. | A¹ | A¹' | R⁸ | R⁹ |
|---|---|---|---|---|
| A-25 | phenyl | phenyl | phenyl | 4-tert-butylphenyl |
| A-26 | 4-methylphenyl | 4-methylphenyl | phenyl | 4-tert-butylphenyl |
| A-27 | 3-methylphenyl | 3-methylphenyl | phenyl | 4-tert-butylphenyl |
| A-28 | 2-methylphenyl | 2-methylphenyl | phenyl | 4-tert-butylphenyl |
| A-29 | phenyl | 1-naphthyl | phenyl | 4-tert-butylphenyl |
| A-30 | 4-biphenyl | 4-biphenyl | phenyl | 4-tert-butylphenyl |
| A-31 | phenyl | phenyl | phenyl | 4-biphenyl |
| A-32 | 4-methylphenyl | 4-methylphenyl | phenyl | 4-biphenyl |
| A-33 | 3-methylphenyl | 3-methylphenyl | phenyl | 4-biphenyl |
| A-34 | 2-methylphenyl | 2-methylphenyl | phenyl | 4-biphenyl |
| A-35 | phenyl | 1-naphthyl | phenyl | 4-biphenyl |

-continued

| Cpd. | A¹ | A¹' | R⁸ | R⁹ |
|---|---|---|---|---|
| A-36 | biphenyl-4-yl | biphenyl-4-yl | phenyl | biphenyl-4-yl |
| A-37 | phenyl | phenyl | 3-(trifluoromethyl)phenyl | phenyl |
| A-38 | 4-methylphenyl | 4-methylphenyl | 3-(trifluoromethyl)phenyl | phenyl |
| A-39 | 3-methylphenyl | 3-methylphenyl | 3-(trifluoromethyl)phenyl | phenyl |
| A-40 | 2-methylphenyl | 2-methylphenyl | 3-(trifluoromethyl)phenyl | phenyl |
| A-41 | phenyl | naphthalen-1-yl | 3-(trifluoromethyl)phenyl | phenyl |
| A-42 | biphenyl-4-yl | biphenyl-4-yl | 3-(trifluoromethyl)phenyl | phenyl |
| A-43 | phenyl | naphthalen-1-yl | phenyl | naphthalen-1-yl |
| A-44 | phenyl | naphthalen-2-yl | phenyl | naphthalen-1-yl |

-continued

| Cpd. | A¹ | A¹' | R⁸ | R⁹ |
|---|---|---|---|---|
| A-45 | 1) | 1) | 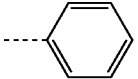 | 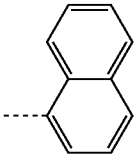 | wherein

1) -NA¹A¹' is 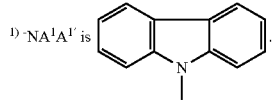.

17. The device of claim 2, wherein the hole transporting/injecting layer (b) comprises the compound of formula (I) and a dopant, and the dopant is at least one selected from the group consisting of titanium oxide ($TiO_x$), vanadium oxide ($VO_x$), molybdenium oxide ($MoO_3$), especially $MO_3$, tungsten oxide ($WO_x$), ruthenium oxide ($RuO_x$), chromium oxide ($CrO_x$), zirconium oxide ($ZrO_x$), hafnium oxide ($HfO_x$) tantalum oxide ($TaO_x$), silver oxide ($AgO_x$), manganese oxide ($MnO_x$), iron trichloride ($FeCl_3$), antimony pentachloride ($SbCl_5$), a metal phthalocyanine compound, dicyano(phthalocyanato(−1)cobalt(III), a oxocarbon-, pseudooxocarbon- or radialene compound, a dicyano(phthalocyanato(−1)ruthenium(III) compound, 2-(6-dicyanomethylene-1,3,4,5,7,8-hexafluoro-6H-naphthalen-2-ylidene)-malononitrile,

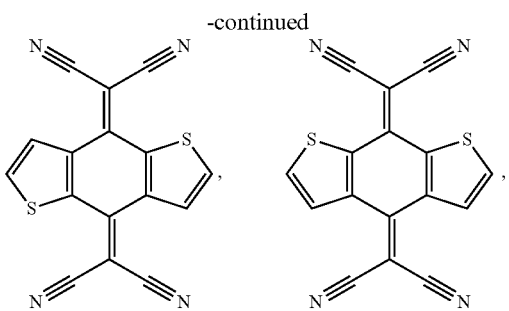

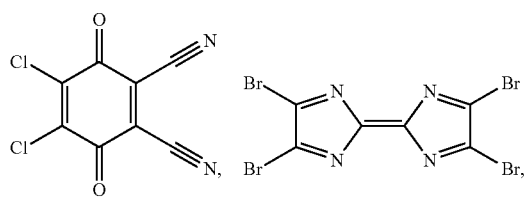

2,3,5,6-tetrafluoro-7,7,8,8-tetracyanoquinodimethane (F₄-TCNQ),

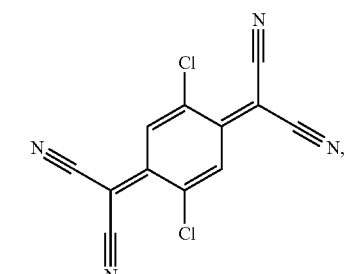

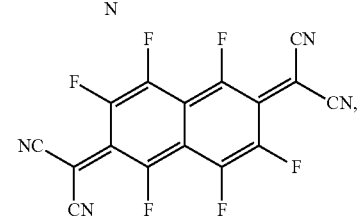

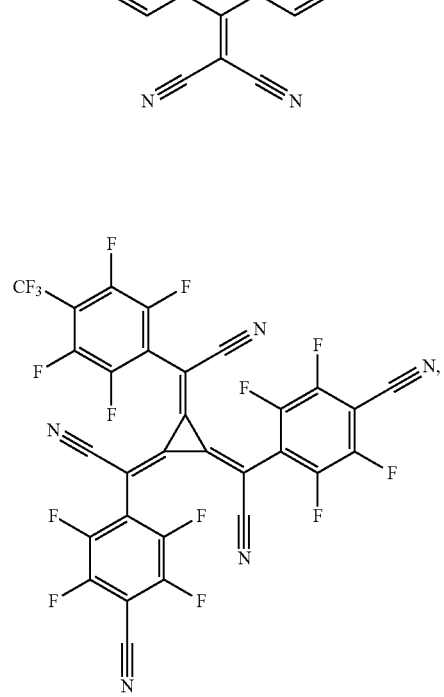

75
-continued
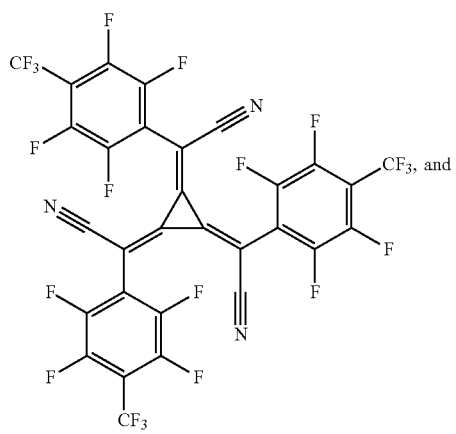
76
-continued
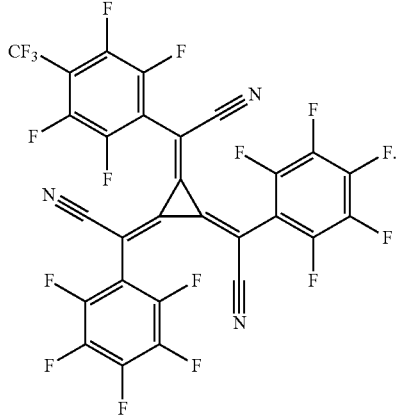
* * * * *